(12) United States Patent
Shimizu et al.

(10) Patent No.: US 8,449,458 B2
(45) Date of Patent: May 28, 2013

(54) BODY-INSERTABLE APPARATUS AND RADIO IN-VIVO INFORMATION ACQUIRING SYSTEM

(75) Inventors: Hatsuo Shimizu, Hachioji (JP); Seiichiro Kimoto, Hachioji (JP); Takemitsu Honda, Hino (JP); Takeshi Mori, Machida (JP); Noriyuki Fujimori, Suwa (JP)

(73) Assignee: Olympus Corporation (JP)

( * ) Notice: Subject to any disclaimer, the term of this patent is extended or adjusted under 35 U.S.C. 154(b) by 1691 days.

(21) Appl. No.: 11/571,504

(22) PCT Filed: Feb. 25, 2005

(86) PCT No.: PCT/JP2005/003191
§ 371 (c)(1),
(2), (4) Date: Jul. 25, 2007

(87) PCT Pub. No.: WO2006/090472
PCT Pub. Date: Aug. 31, 2006

(65) Prior Publication Data
US 2008/0045792 A1    Feb. 21, 2008

(51) Int. Cl.
*A61B 1/06* (2006.01)
(52) U.S. Cl.
USPC ........................................ 600/160
(58) Field of Classification Search
USPC ................. 600/117–118, 109, 160, 178, 302
See application file for complete search history.

(56) References Cited

U.S. PATENT DOCUMENTS

| 5,469,840 | A | * | 11/1995 | Tanii et al. | 600/117 |
| 2004/0109488 | A1 | | 6/2004 | Glukhovsky et al. | 374/120 |
| 2004/0111011 | A1 | * | 6/2004 | Uchiyama et al. | 600/160 |
| 2004/0193010 | A1 | | 9/2004 | Fujimori et al. | 600/118 |
| 2007/0066868 | A1 | * | 3/2007 | Shikii | 600/118 |
| 2007/0221233 | A1 | * | 9/2007 | Kawano et al. | 128/899 |
| 2007/0282164 | A1 | * | 12/2007 | Frisch et al. | 600/109 |
| 2008/0177136 | A1 | * | 7/2008 | Wang | 600/109 |
| 2009/0306632 | A1 | * | 12/2009 | Trovato et al. | 604/890.1 |
| 2009/0306633 | A1 | * | 12/2009 | Trovato et al. | 604/891.1 |

FOREIGN PATENT DOCUMENTS

| JP | 8-248326 | 9/1996 |
| JP | 2003-144385 | 5/2003 |
| JP | 2004-236167 | 8/2004 |
| WO | 96/41119 | 12/1996 |
| WO | WO 01/35813 | 5/2001 |
| WO | WO01/35813 | 5/2001 |
| WO | 03/096889 | 11/2003 |

OTHER PUBLICATIONS

Extended European Search Report for corresponding European Application No. 10 01 5744 mailed Feb. 23, 2011.
European Search Report dated Feb. 8, 2010.
International Search Report and Written Opinion dated Mar. 29, 2005 issued in corresponding PCT Application No. PCT/JP2005/003191.

* cited by examiner

*Primary Examiner* — Philip R Smith
(74) *Attorney, Agent, or Firm* — Ostrolenk Faber LLP

(57) ABSTRACT

A body-insertable apparatus that is used in a state of being introduced inside the body of a subject and that executes a predetermined function inside the body of the subject, comprises a driving controller that controls the driving condition of the predetermined function.

1 Claim, 22 Drawing Sheets

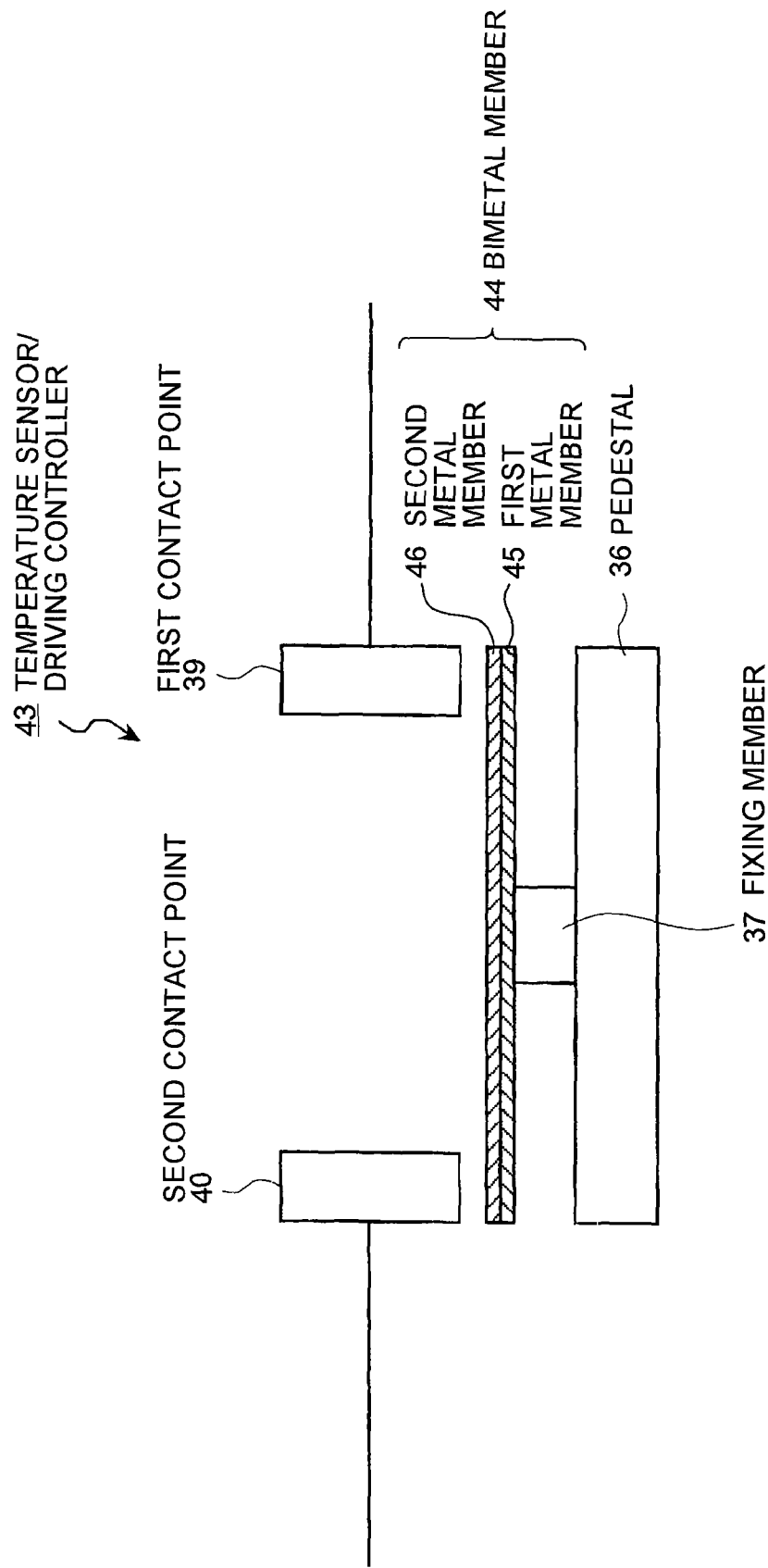

BODY-INSERTABLE APPARATUS AND RADIO IN-VIVO INFORMATION ACQUIRING SYSTEM

CROSS REFERENCE TO RELATED APPLICATION

The present application is a 35 U.S.C. §§371 national phase conversion of PCT/JP2005/003191, filed 25 Feb. 2005, which is herein incorporated by reference.

TECHNICAL FIELD

The present invention relates to a body-insertable apparatus serving as a radio in-vivo information acquiring apparatus that is used in a state of being introduced inside a body of a subject and that executes a predetermined function, and a radio in-vivo information acquiring system using the body-insertable apparatus system.

BACKGROUND ART

Recently, in the field of endoscope, a swallowable capsule endoscope equipped with an imaging function and a radio communication function has appeared. The capsule endoscope is configured to take images during an observation period after the capsule endoscope is swallowed by an examinee as a subject for observation (examination) until naturally discharged from a body of the examinee, sequentially while passing through internal organs (inside body cavities) such as a stomach and a small intestine according to the peristalsis thereof.

Moreover, image data obtained inside the body cavities by the capsule endoscope during this observation period while moving inside these organs is sequentially transmitted to an external device provided outside the subject by radio communication based on a predetermined sequence, and stored in a memory. If the examinee carries the external device having this radio communication function and the memory function, the examinee can freely move without having any inconveniences during the period from swallow of the capsule endoscope until discharge thereof. After the image data is acquired, doctors or nurses can perform diagnosis based on the image data stored in the memory of the external device by displaying an image of the body cavities on a display unit such as a display.

To control activation of the capsule endoscope, such a configuration has been proposed that a lead switch to turn on and off by an external magnetic field is provided in the capsule endoscope, and a permanent magnet to supply a magnetic field is provided to a package of the capsule endoscope. Specifically, the lead switch provided in the capsule endoscope has a configuration so that the lead switch maintains an off state under an environment in which the external magnetic field having intensity higher than predetermined intensity is applied, and switches to turn on when the intensity of the external magnetic field is lowered. Therefore, in a state of being packed in the package before being swallowed, power supply from a power source such as a battery to electric components of a device or the like having the imaging function and the radio communication function is cut by this magnet, and the capsule endoscope is not activated, thereby preventing waste of the battery. On the other hand, at the time of being swallowed, the capsule endoscope is unpacked from the package to be separated from the permanent magnet and released from the influence of the magnetic force, and the power supply cut to the electric components is canceled. Thus, power is supplied to the above electric components of the capsule endoscope, and acquisition and transmission of images are performed. With this configuration, it is possible to prevent actuation of the capsule endoscope while the capsule endoscope is packed in the package (For example, see FIG. 1).

Patent Document 1: International Publication No. WO/0135813 Pamphlet

Problem to be Solved by the Invention

However, even with a mechanism to control a driving state of the capsule endoscope as described above, the actuation of the capsule endoscope outside of the body of the subject is not fully prevented. In other words, since it requires some time until the capsule endoscope is introduced inside the body of the subject after the capsule endoscope is taken out of the package, the capsule endoscope starts driving before introduction into the body of the subject. Problems occurring when the capsule endoscope starts driving before introduction into the body of the subject will be explained below.

First, unnecessary image data, which is not used for diagnosis and the like, is acquired due to actuation of the capsule endoscope before being introduced into the body of the subject. The capsule endoscope is configured to start imaging upon actuation, and to transmit acquired image data by radio communication. Therefore, if actuated before being introduced into the body of the subject, the capsule endoscope starts an imaging operation and the like outside the body of the subject.

As a result, great amount of image data is acquired before the capsule endoscope is introduced inside the body of the subject after a capsule is unpacked, and therefore, doctors and the like are required to delete the unnecessary data to perform the diagnosis or the like. Since an imaging rate of the capsule endoscope is set such that, for example, two shots are taken per second, even in a short time of about several tens of seconds, if the capsule endoscope is actuated outside the body of the subject, great amount of unnecessary image data is acquired. Therefore, to prevent acquisition of such unnecessary image data, it is necessary to prevent actuation of the capsule endoscope before being introduced inside the body of the subject.

Moreover, since the acquisition of the unnecessary image data requires a certain amount of driving power, power is supplied to each electric part before the capsule endoscope is introduced into the body of the subject. Especially, if power is supplied to a radio device of which power consumption is high, at an early stage in the period before introduction into the body of the subject, power of a battery can be exhausted to stop power supply before image collection is sufficiently performed at an organ for which imaging is necessary to be done. Therefore, also in terms of power consumption, it is necessary to prevent actuation of the capsule endoscope before being introduced into the body of the subject.

The above problems can occur even when the capsule endoscope is discharged from the body again without exhausting power inside the body of the subject. Therefore, a practical application of a capsule endoscope that does not operate before being introduced into the body of the subject and after being discharged from the body of the subject and a system using the capsule endoscope is strongly demanded.

The present invention has been achieved in view of the above problems, and it is an object of the present invention to provide a body-insertable apparatus, such as a capsule endoscope, in which unintentional driving outside of the body of the subject is prevented and a radio in-vivo information acquiring system using the body-insertable apparatus.

Moreover, it is another object of the present invention to provide a body-insertable apparatus with which collection and transmission of images of the inside of the body of a subject are accurately performed while reducing unnecessary power consumption by controlling power supply timing to a radio device to be after introduction of a capsule endoscope into the body of the subject.

Means for Solving Problem

A body-insertable apparatus according to one aspect of the present invention is used in a state of being introduced inside a body of a subject, executes a predetermined function inside the body of the subject, and includes a driving controller that controls a driving condition of the predetermined function.

Moreover, the body-insertable apparatus may further include a function executing unit that executes the predetermined function; and a temperature sensor unit that detects a temperature that fluctuates according to a temperature change of an ambient environment of the body-insertable apparatus, wherein the driving controller may control a driving condition of the function executing unit based on the temperature detected by the temperature sensor unit. According to the body-insertable apparatus as above, since the driving condition of the function executing unit is controlled based on the temperature detected by the temperature detector, it is possible to start driving, for example, based on a temperature change at the time of introduction into the inside of the body of the subject form the outside of the body of the subject.

Furthermore, in the body-insertable apparatus, the driving controller may control the function executing unit to drive when the temperature detected by the temperature sensor unit increases to a value equal to or higher than a predetermined threshold temperature.

Moreover, in the body-insertable apparatus, the driving controller may stop the driving of the function executing unit when the temperature detected by the temperature sensor unit decreases to a value lower than a predetermined threshold temperature.

Furthermore, in the body-insertable apparatus, the predetermined threshold temperature may be a temperature higher than a temperature outside the body of the subject and equal to or lower than a body temperature of the subject.

Moreover, in the body-insertable apparatus, the function executing unit may execute the predetermined function based on supplied driving power, and the driving controller may control the driving condition of the function executing unit by controlling supply of the driving power to the function executing unit.

Furthermore, in the body-insertable apparatus, the temperature sensor unit and the driving controller may be integrally formed, and the temperature sensor unit and the driving controller integrally formed may include a first contact point that is electrically connected to a power source, a second contact point that is electrically connected to the function executing unit, and a shape-memory member that is arranged near the first contact point and the second contact point, that has a critical temperature equal to a threshold temperature, and that transforms into a shape at a temperature equal to or higher than the critical temperature so as to contact the first contact point and the second contact point.

Moreover, in the body-insertable apparatus, the temperature sensor unit and the driving controller may be integrally formed, and the temperature sensor unit and the driving controller integrally formed may include a first contact point that is electrically connected to a power source, a second contact point that is electrically connected to the function executing unit, and a bimetal member that is arranged near the first contact point and the second contact point, and that is formed so as to contact the first contact point and the second contact point at a temperature equal to a threshold temperature.

Furthermore, the body-insertable apparatus may include a heat-conduction inhibiting member arranged to cover at least the temperature sensor unit.

Moreover, in the body-insertable apparatus, the function executing unit may include an imaging unit that acquires image data of inside of the subject, and a radio unit that transmits the image data acquired by the imaging unit to outside by radio communication.

Furthermore, the body-insertable apparatus include an information acquiring unit that acquires in-vivo information of an examined area inside the body of the subject; a radio unit that modulates a signal relating to the in-vivo information, the signal generated by the information acquiring unit, to transmit the modulated signal by radio communication; a power source unit that accumulates driving power to drive the information acquiring unit and the radio unit; and a detector that detects distance to the examined area, wherein the driving controller may include a supply controller that controls supply of the driving power from the power source unit to the radio unit based on a result of detection by the detector.

Moreover, the body-insertable apparatus may further include an illuminating unit that emits illuminating light to illuminate the examined area, wherein the detector may detect the distance to the examined area based on an amount of light reflected from the examined area of the light emitted from the illuminating unit.

Furthermore, in the body-insertable apparatus, the supply controller may make the power source unit start supplying the driving power to the radio unit in response to the detector detecting that the distance to the examined area becomes less than a predetermined set value.

Moreover, in the body-insertable apparatus, the information acquiring unit may be an imaging unit that generates an image signal by imaging the examined area illuminated by the illuminating unit.

Furthermore, in the body-insertable apparatus, the imaging unit may image an imaging subject surface positioned away from the imaging unit for a known predetermined distance, and the detector may detect the distance to the examined area to be imaged by the imaging unit, based on the distance from the imaging unit to the imaging subject surface which the imaging unit has imaged.

Moreover, in the body-insertable apparatus, the imaging unit may further include an automatic focusing unit, and an operation controller that controls an automatic focus operation of the automatic focusing unit based on the image signal generated by the imaging unit, and the detector may detect the distance to the examined area based on an operating condition of the automatic focusing unit.

Furthermore, the body-insertable apparatus may include a function executing unit that executes the predetermined function; and a photoelectric converter of which intensity of dark current is temperature dependent, wherein the driving controller may control the driving condition of the function executing unit based on the intensity of the dark current of the photoelectric converter. According to the body-insertable apparatus as above, since the driving condition is controlled utilizing temperature dependence of the intensity of the dark current in the photoelectric converter, it is possible to control the driving condition based on the temperature of the body-insertable apparatus.

Moreover, in the body-insertable apparatus, the driving controller may control, when the intensity of the dark current is lower than a threshold intensity, to stop driving of the function executing unit.

Furthermore, the body-insertable apparatus may include an illuminating unit that emits illuminating light to illuminate inside of the body of the subject; a plurality of photoelectric converters that are arranged in matrix; an imaging unit that acquires image information of the inside of the body of the subject illuminated by the illuminating unit; and a radio unit that transmits the image information acquired by the imaging unit to outside by radio communication, wherein the driving controller may control a driving condition of at least one of the illuminating unit and the radio unit, based on a temperature characteristic of the intensity of the dark current obtained in one or more of the photoelectric converters. According to the body-insertable apparatus as above, since the driving condition is controlled utilizing the temperature dependence of the intensity of the dark current in the photoelectric converter that is provided in the imaging unit, it is possible to control the driving condition based on the temperature of the body-insertable apparatus, and to perform driving condition control with a simple configuration by applying existing components.

Moreover, in the body-insertable apparatus, the driving controller may control the driving condition based on a number of the photoelectric converters in which the intensity of the dark current is equal to or higher than a predetermined threshold intensity.

Furthermore, in the body-insertable apparatus, the driving controller may control, when the number of the photoelectric converters in which the intensity of the dark current is equal to or higher than the predetermined threshold intensity becomes smaller than a predetermined number, to stop the driving of at least the radio unit.

Moreover, in the body-insertable apparatus, the predetermined number may be determined based on the temperature inside the body of the subject.

Furthermore, in the body-insertable apparatus, the driving controller may control to stop the driving of at least the radio unit, when the intensity of the dark current of at least one of specific photoelectric converters among the photoelectric converters constituting the imaging unit is lower than the predetermined threshold intensity.

Moreover, in the body-insertable apparatus, the threshold intensity may be intensity higher than intensity of the dark current at a temperature outside the body of the subject and equal to or lower than intensity of the dark current at a temperature inside the body of the subject.

Furthermore, in the body-insertable apparatus, the photoelectric converter may be configured to include a photodiode.

Moreover, a radio in-vivo information acquiring system according to another aspect of the present invention includes a body-insertable apparatus that is introduced inside a body of a subject, and a receiving device that is arranged outside the body of the subject and that acquires information acquired by the body-insertable apparatus by radio communication, wherein the body-insertable apparatus includes a function executing unit that executes a predetermined function based on driving power supplied, a radio unit that transmits information acquired by the function executing unit, by radio communication; and a driving controller that controls a driving condition of the function executing unit, and the receiving device includes a radio receiving unit that receives the information transmitted from the radio unit, and a processor that analyzes the received information.

Furthermore, in the radio in-vivo information acquiring system, invention, the body-insertable apparatus may further include a temperature sensor unit that detects a temperature that fluctuates according to a temperature change of an ambient environment of the body-insertable apparatus, and the driving controller may control the driving condition of the function executing unit based on the temperature acquired by the temperature sensor unit.

Moreover, in the radio in-vivo information acquiring system, the function executing unit may include a photoelectric converter in which intensity of the dark current is temperature dependent, the radio unit may transmit the image data acquired by the imaging unit to the outside by radio communication, and the driving controller may set a threshold temperature at a temperature higher than a temperature outside the body of the subject and equal to or lower than a temperature of the body of the subject, and may control such that the imaging unit and the radio unit drive at a temperature equal to or higher than the threshold temperature.

Furthermore, in the radio in-vivo information acquiring system, the body-insertable apparatus may further include a photoelectric converter in which intensity of dark current is temperature dependent, and the driving controller may control the driving condition of the function executing unit based on the intensity of the dark current in the photoelectric converter.

Moreover, in the radio in-vivo information acquiring system, the body-insertable apparatus may include an illuminating unit that emits illuminating light to illuminate inside of the body of the subject; and an imaging unit that includes a plurality of photoelectric converters arranged in matrix, and that acquires image information of the inside of the body of the subject illuminated by the illuminating unit, the radio unit may transmit the image information acquired by the imaging unit to outside, by radio communication, and the driving controller may control a driving condition of at least one of the illuminating unit and the radio unit based on a temperature characteristic of intensity of dark current obtained in one or more of the photoelectric converters.

Effect of the Invention

Since a body-insertable apparatus and a radio in-vivo information acquiring system according to the present invention are configured to control a driving state of a function executing unit based on a temperature detected by a temperature sensor unit, it is possible to start driving based on, for example, a change in temperature at the time of introduction into the inside of the body of a subject from the outside of the body of the subject, thereby preventing actuation of the body-insertable apparatus outside the body of the subject.

Since the body-insertable apparatus according to the present invention detects distance to an examined area, and detects whether the apparatus is located inside a body cavity based on the detected distance to determine power supply to a radio device, it is possible to control power supply timing to the radio device to be after introduction into the body of the subject, thereby reducing unnecessary power consumption and accurately performing collection and transmission of images inside the subject.

Since the body-insertable apparatus according to the present invention detects distance to an imaging subject based on a relationship between reflected light amount and distance, and detects whether the apparatus is located inside a body cavity based on the detected distance to determine power supply to a radio device, it is possible to control power supply timing to the radio device to be after introduction into the body of the subject, thereby reducing unnecessary power consumption and accurately performing collection and transmission of images inside the subject.

Since the body-insertable apparatus according to the present invention detects distance to an imaging subject based on control of an automatic focus operation of an automatic focusing function, and detects whether the apparatus is located inside a body cavity based on the detected distance to determine power supply to a radio device, it is possible to control power supply timing to the radio device to be after introduction into the body of the subject, thereby reducing unnecessary power consumption and accurately performing collection and transmission of images inside the subject.

Since a body-insertable apparatus and a radio in-vivo information acquiring system according to the present invention are configured to control a driving state of a function executing unit based on a temperature detected by a temperature sensor unit, it is possible to start driving based on, for example, a change in temperature at the time of introduction into the inside of the body of a subject from the outside of the body of the subject, thereby preventing actuation of the body-insertable apparatus outside the body of the subject.

BRIEF DESCRIPTION OF DRAWINGS

FIG. 6-B is a schematic diagram showing a state of the temperature sensor/driving controller under a temperature lower than a threshold temperature;

FIG. 7 is a schematic diagram showing a configuration of a temperature sensor/driving controller provided in the capsule endoscope according to a second example of the first embodiment;

FIG. 8-B is a schematic diagram showing a state of the temperature sensor/driving controller under a temperature lower than a threshold temperature;

EXPLANATIONS OF LETTERS OR NUMERALS

Figure 1:
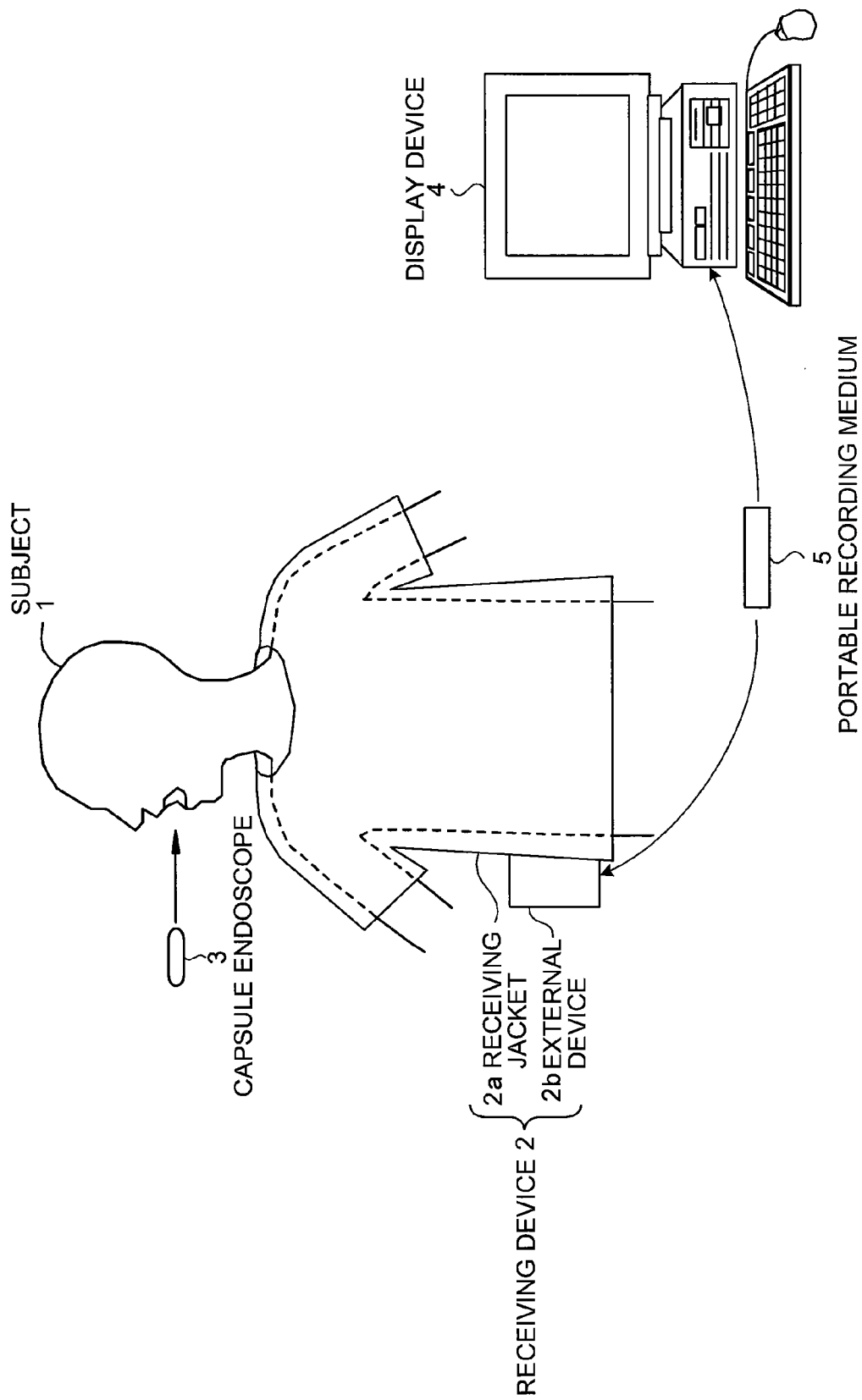
FIG. 1 is a schematic diagram showing an entire configuration of a radio in-vivo information acquiring system according to a first embodiment.

1 Subject
2 Receiving device
2a Receiving jacket
2b External device
3, 132, 137, 143 Capsule endoscope (Body-insertable apparatus)
4 Display device
5 Portable recording medium
11 RF receiving unit
12 Image processing unit
13 Storage unit
18 Power supply unit
19 LED (Illuminating unit)
20 LED driving circuit
21 CCD (Imaging device)
22 CCD driving circuit
23 RF transmitting unit (Radio device)
24 Transmitting antenna unit (Transmitting antenna)
32 System control circuit
33 Temperature sensor unit
34, 141, 145 Driving controller
35 Temperature sensor/driving controller
36 Pedestal
37 Fixing member
38 Temperature transformation member
39 First contact point
40 Second contact point
41, 42 Pulling-force applying member
43 Temperature sensor/driving controller
44 Bimetal member
45 First metal member
46 Second metal member 47 Capsule endoscope
48 Heat-conduction inhibiting member
100 Battery (Power source unit)
111a, 111b Dome
114 Optical system part
119 Lead switch
120 Subswitch
121 Distance sensor
122 Supply controller
123 Latch circuit
124 Timer
125 Light amount sensor
126 Automatic focusing unit
130 Magnet
131 Dome protection cap
133 Dark current detecting unit
135 Photodiode
136 Light shielding member
138 Noise-pixel detecting unit
139 Noise-pixel processing unit
140 Noise-pixel counting unit
144 Reference-pixel-state determining unit
A1 to An Receiving antenna

BEST MODE(S) FOR CARRYING OUT THE INVENTION

A radio in-vivo information acquiring system according to exemplary embodiments of the present invention will be explained below. Note that drawings are schematically shown, a relationship between thickness and width of each part, ratio of thickness of each part differs from actual cases, needless to mention that also among drawings, in some parts, a relationship and ratio of sizes differ therebetween. Moreover, while a first embodiment will be explained in a case of a capsule endoscope that acquires images inside the body cavities below, it is needless to mention that the in-vivo information is not limited to the internal image of the body of the subject, and the radio in-vivo information acquiring system is not limited to the capsule endoscope.

First Embodiment

First, the radio in-vivo information acquiring system according to the first embodiment will be explained. To prevent actuation of the capsule endoscope, as an example of a body-insertable apparatus, outside a body of a subject, the radio in-vivo information acquiring system according to the first embodiment is configured to include a driving state controller that controls a driving state of each component of the capsule endoscope, utilizing difference in temperature the outside and the inside of the body of the subject. More specifically, the driving state controller is configured to drive each component under a condition that the temperature is equal to or higher than a threshold determined based on body temperature of a subject 1.

FIG. 1 is a schematic diagram showing an entire configuration of the radio in-vivo information acquiring system according to the first embodiment. As shown in FIG. 1, the radio in-vivo information acquiring system includes a receiving device 2 that has a radio receiving function and a capsule endoscope 3 that is introduced inside a body of the subject 1, and that acquires images inside body cavities to transmit data to the receiving device 2. Moreover, the radio in-vivo information acquiring system includes a display device 4 that displays the images of the body cavities based on the data received by the receiving device 2, and a portable recording medium 5 to communicate the data between the receiving device 2 and the display device 4. The receiving device 2 includes a receiving jacket 2a worn by the subject 1 and an external device 2b that performs signal processing on the radio signal received through the receiving jacket 2a.

The display device 4 is to display the cavity images acquired by the capsule endoscope 3, and has a configuration similar to a workstation and the like to perform image display based on the data obtained by the portable recording medium 5. Specifically, the display device 4 can take a configuration to directly display the images with a CRT display, a liquid crystal display, and the like, or can take a configuration to output the images to another medium such as a printer or the like.

The portable recording medium 5 is configured to be attachable and detachable to the external device 2b and the display device 4, and to enable output and record of information when attached thereto. Specifically, the portable recording medium 5 is attached to the external device 2b while the capsule endoscope 3 is changing position thereof inside the body cavities of the subject 1, and records data that is transmitted from the capsule endoscope 3. Then, after the capsule endoscope 3 is discharged from the subject 1, in other words, when the in-vivo imaging is completed, the portable recording medium 5 is detached from the external device 2b and attached to the display device 4 so that the data recorded therein is read out by the display device 4. By applying the portable recording medium 5 such as a compact flash (registered trademark) memory and the like to perform communication of the data between the external device 2b and the display device 4, unlike the case in which the external device 2b and the display device 4 are linked by wired connection, the subject 1 can freely move even while in-vivo imaging is being performed.

Figure 2:
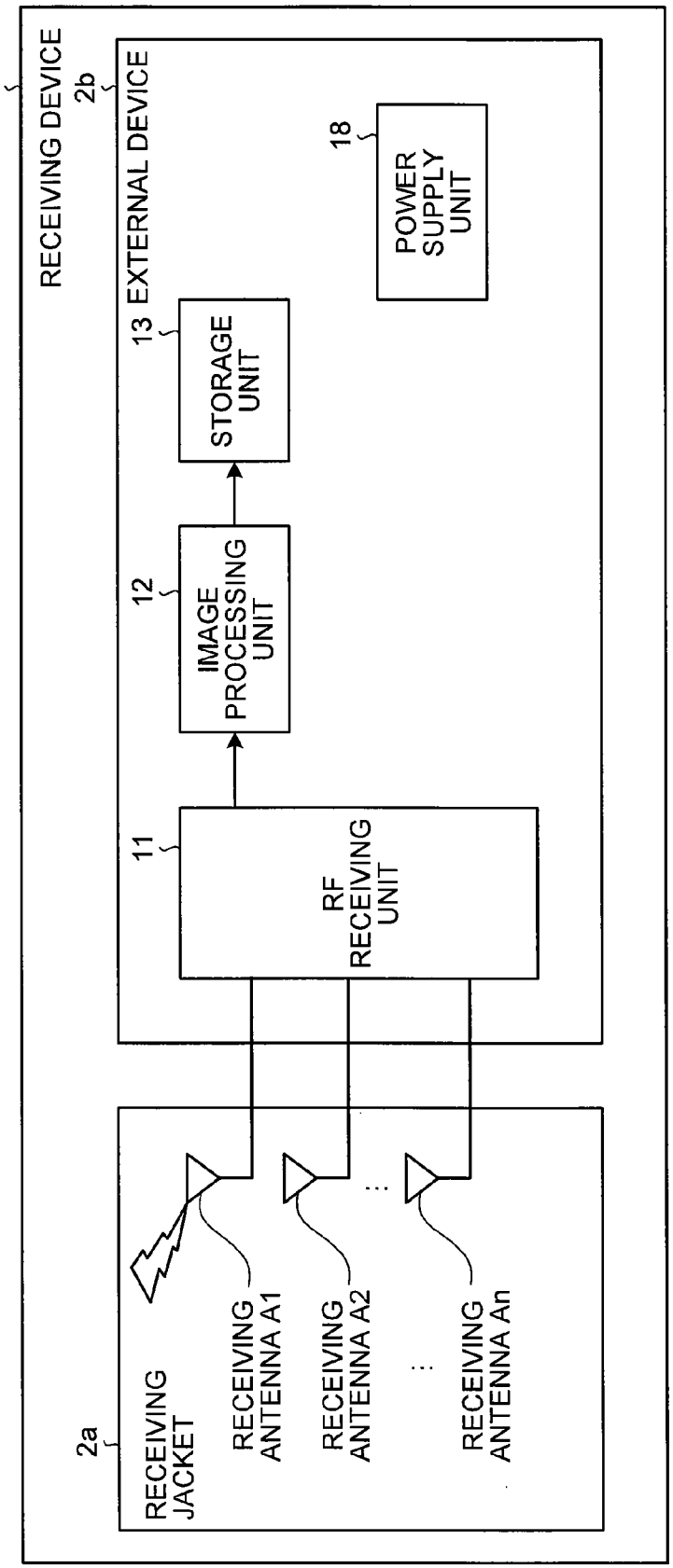
FIG. 2 is a block diagram schematically showing a configuration of a receiving device constituting the radio in-vivo information acquiring system.

The receiving device 2 has a function of receiving the cavity image data transmitted by radio from the capsule endoscope 3. FIG. 2 is a block diagram schematically showing a configuration of the receiving device 2. As shown in FIG. 2, the receiving device 2 has a form wearable by the subject 1, and includes the receiving jacket 2a to which receiving antennas A1 to An are provided, and the external device 2b that performs signal processing of the radio signal received.

The external device 2b has a function of processing the radio signal that is transmitted from the capsule endoscope 3. Specifically, as shown in FIG. 2, the external device 2b includes an RF receiving unit 11 as a radio receiving unit that demodulates the radio signal received through the receiving antennas A1 to An, an image processing unit 12 as processing means for performing necessary processing on the image data demodulated, and a storage unit 13 as a storing unit to store the image data that has been subjected to the image processing. Through the storage unit 13, the image data is recorded in the portable recording medium 5.

Figure 3:
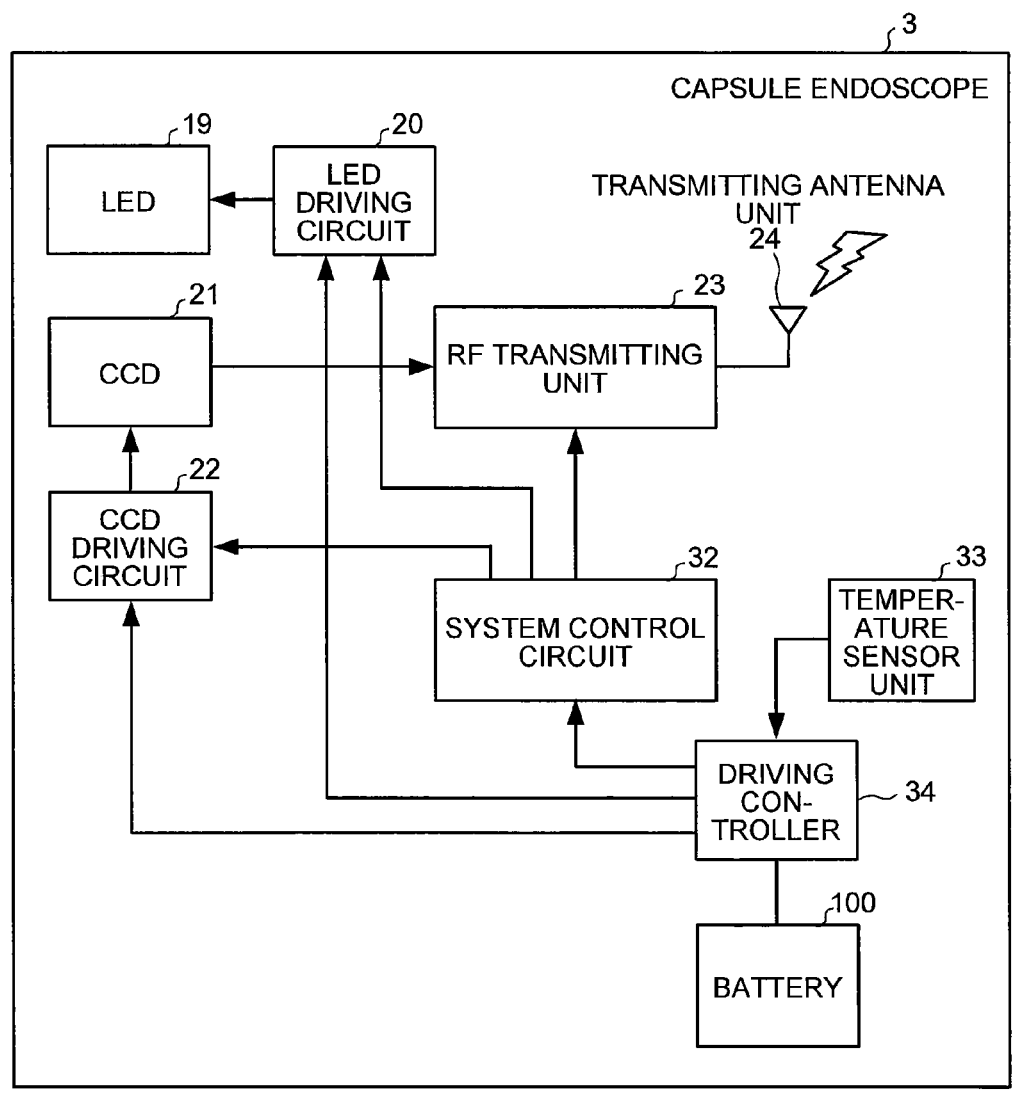
FIG. 3 is a block diagram schematically showing a configuration of a capsule endoscope constituting the radio in-vivo information acquiring, system according to the first embodiment.

The capsule endoscope 3 will be explained next. FIG. 3 is a block diagram schematically showing a configuration of the capsule endoscope 3. As shown in FIG. 3, the capsule endoscope 3 includes an LED 19 as an illuminating unit to illuminate an imaging area at the time of imaging the inside of the subject 1, an LED driving circuit 20 that controls a driving condition of the LED 19, and a CCD 21 as a photoelectric converter that generates image data by acquiring reflected light images from the area illuminated by the LED 19 or an imaging unit. Furthermore, the capsule endoscope 3 includes a CCD driving circuit 22 that controls a driving condition of the CCD 21, an RF transmitting unit 23 that generates an RF signal by modulating the image data acquired by the CCD 21, a transmitting antenna unit 24 as a radio communication unit to transmit by radio the RF signal output by the RF transmitting unit 23, and an operation controller 32 as an operation control unit that controls operations of the LED driving circuit 20, a CCD driving circuit 22, and the RF transmitting unit 23.

With these mechanisms provided, the capsule endoscope 3 acquires, by the CCD 21, image data of a subject area illuminated by the LED 19 while the capsule endoscope 3 is introduced inside the subject 1. The acquired image data is converted into an RF signal by the RF transmitting unit 23 to be transmitted to the outside through the transmitting antenna unit 24.

Furthermore, the capsule endoscope 3 includes a battery 100 as a power source unit to drive internal components of the capsule endoscope 3, such as the LED driving circuit 20, the CCD driving circuit 22, and the RF transmitting unit 23 as function executing units that respectively executes predetermined functions. The system control circuit 32 controls operating conditions of the LED driving circuit 20, the CCD driving circuit 22, the RF transmitting unit, and the like, more specifically, operation of the function executing unit such as an illuminating period of the LED 19, a frame rate of the CCD 21, transmission timing of the RF signal or the like based on a predetermined information. The capsule endoscope 3 further includes a temperature sensor unit 33 and a driving controller 34 serving as a driving control unit that controls driving conditions of the LED driving circuit 20, the CCD driving circuit 22, the system control circuit 32, and the like based on the temperature detected by the temperature sensor unit 33.

The temperature sensor unit 33 and the driving controller 34 provided in the capsule endoscope 3 will be explained next. As shown in FIG. 3, in the first embodiment, the capsule endoscope 3 is configured to have the driving controller 34 arranged between the system control circuit 32 and the battery 100, and the driving controller 34 is configured to control driving conditions of components in the capsule endoscope 3 based on an output signal from the temperature sensor unit 33.

The temperature sensor unit 33 is to detect a temperature inside the capsule endoscope 3 that fluctuates according to temperature of ambient around the capsule endoscope 3. The temperature sensor unit 33 has, for example, a function of repeating temperature detection at predetermined time intervals and of outputting data to the driving controller 34. It is preferable to set a threshold temperature to a value lower than the temperature detected by the temperature sensor unit 33 when the capsule endoscope 3 is introduced inside the subject 1, near the detected temperature, and higher than, for example, temperature of about room temperature. Specifically, for example, when the subject 1 is a human body, it is preferable to set the threshold temperature at around 34.5° C., which is a bit lower than body temperature.

The driving controller 34 controls driving conditions of components of the capsule endoscope 3 based on a signal output from the temperature sensor unit 33. Specifically, the driving controller 34 performs such a control that for example, when the temperature detected by the temperature sensor unit 33 is equal to or higher than the threshold, the components in the capsule endoscope 3 are turned into an on state, and when the temperature becomes lower than the threshold, the components are turned into an off state. Although shown as separate components in the configuration shown in FIG. 3, the temperature sensor unit 33 and the driving controller 34 can be integrally formed, as described later.

Figure 4:
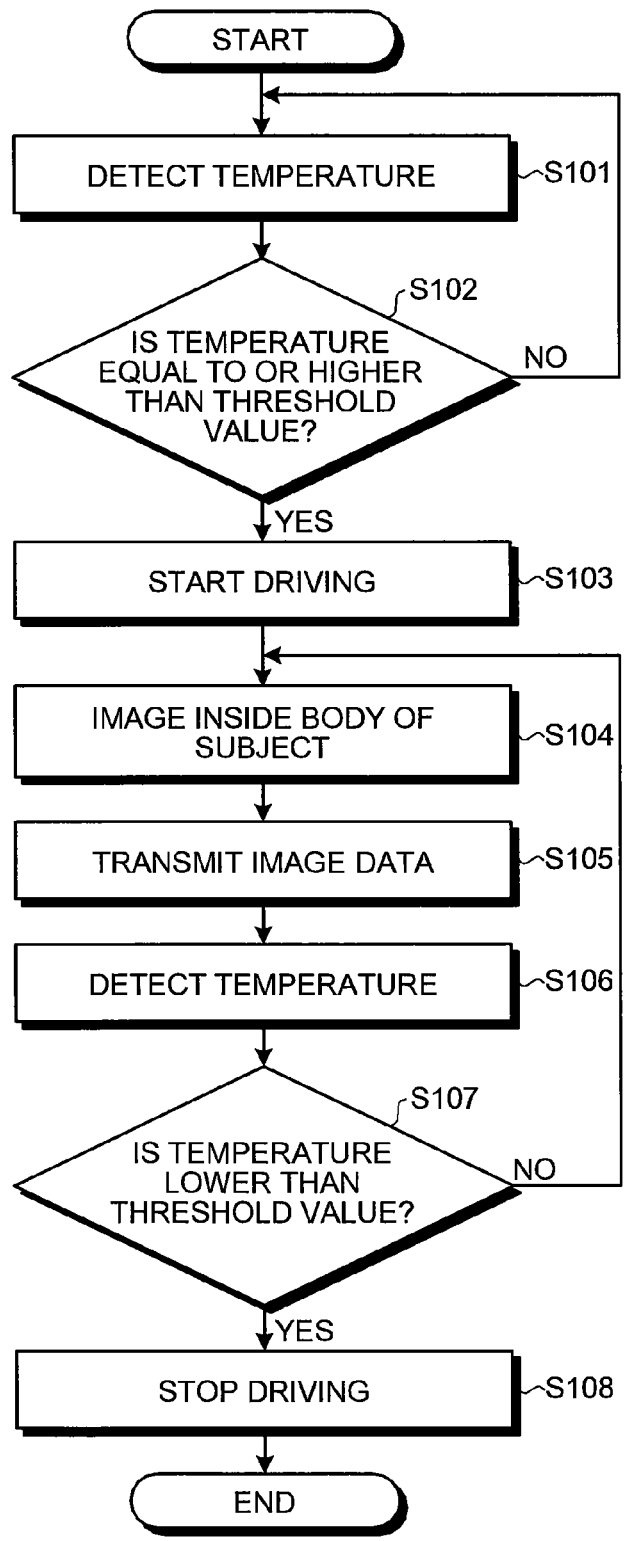
FIG. 4 is a flowchart for explaining an operation of the capsule endoscope.

An operation of the capsule endoscope 3 according to the first embodiment will be explained next. FIG. 4 is a flowchart for explaining the operation of the capsule endoscope 3 according to the first embodiment, and explanations will be given with reference to FIG. 4. Suppose at the point of START in the flowchart shown FIG. 4, the components in the capsule endoscope 3 are maintained in the off state.

First, the temperature sensor unit 33 performs temperature detection, and outputs temperature information obtained by the detection to the driving controller 34 (step S101). The driving controller 34 determines whether the temperature acquired as a result of the temperature detection is equal to or higher than the threshold (step S102). When it is determined that the temperature acquired as a result of the detection is lower than the threshold, the process returns to step S101 and repeats the operation described above.

When it is determined that the temperature acquired as a result of the temperature detection is equal to or higher than the threshold, the driving controller 34 supplies power accumulated in the battery 100 to the components in the capsule endoscope 3 such as the system control circuit 32 to actuate each component (step S103). In other words, the driving controller 34 determines that the capsule endoscope 3 has been introduced inside the body of the subject based on the temperature being equal to or higher than the threshold, and supplies power accumulated in the battery 100 to each component based on such determination.

The LED 19 emits illumination light to illuminate inside the body of the subject 1, and the CCD 21 performs an imaging operation based on a feedback light of the emitted light (step S104). Image data acquired by the CCD is transmitted to the RF transmitting unit 23, and after subjected to a predetermined modulation operation and the like, the image data is transmitted to the outside through the transmitting antenna unit 24 (step S105). The transmitted image data is received by a receiving mechanism provided in the receiving jacket 2a, and then, provided to the display device 4 through the portable recording medium 5 to be displayed on a screen of the display device 4 as the internal image of the subject.

The temperature detection is again performed by the temperature sensor unit 33, and the temperature data is output to the driving controller 34 (step S106). The driving controller 34 determines whether temperature acquired as a result of the temperature detection is lower than the threshold (step S107). When it is determined that the temperature is not lower than the threshold, it can be determined that the capsule endoscope 3 is still inside the body of the subject 1. Therefore, the process returns back to step S104 again, and the operation at steps S104 to S106 is repeated.

When it is determined that the temperature is lower than the threshold, the driving controller 34 stops supply of power to the components in the capsule endoscope 3 to stop driving of the components (step S108). Since the threshold temperature is set to a temperature lower than body temperature of the subject 1, when the temperature acquired as a result of detection is lower than the threshold, it can be determined that the capsule endoscope 3 has been discharged from the subject 1. Thus, the operation of the capsule endoscope 3 according to the first embodiment is finished.

As described above, in the first embodiment, it is configured to control actuation and termination in driving of the capsule endoscope 3 based on a temperature detected by a temperature sensor provided in the capsule endoscope 3. Advantages of this configuration will be explained below.

First, since the driving condition is controlled based on the detected temperature, it is possible to prevent actuation of the capsule endoscope 3 outside the body of the subject 1. The temperature detected by the temperature sensor unit 33 exceeds the threshold only when the capsule endoscope 3 is introduced inside the body of the subject 1. Therefore, by detecting the temperature with the temperature sensor unit 33, it becomes possible to directly detect whether the capsule endoscope 3 has been introduced inside the body of the subject 1, and by driving the capsule endoscope 3 based on the temperature, it is possible to drive the capsule endoscope 3 only while being introduced inside the subject 1. Furthermore, by preventing the capsule endoscope 3 from driving outside the subject 1, it is possible to prevent acquisition of image data of the outside of the subject 1, which cannot be used for diagnosis or the like, and to prevent unnecessary power consumption.

Moreover, the radio in-vivo information acquiring system according to the first embodiment has an advantage in that such a mechanism can be realized that operations are performed only inside the body of the subject 1, with a simple configuration. Specifically, by applying a shape-memory alloy member, bimetal member, or the like that physically change the shape thereof according to a change in temperature, it is possible to realize a structure simple and quickly adaptable to a temperature change. Furthermore, by providing such member in a switching mechanism, it is possible to realize such a configuration that the temperature sensor unit 33 and the driving controller 34 are integrated, and to drive the temperature sensor unit 33 and the driving controller 34 without supplying power.

Figure 5:
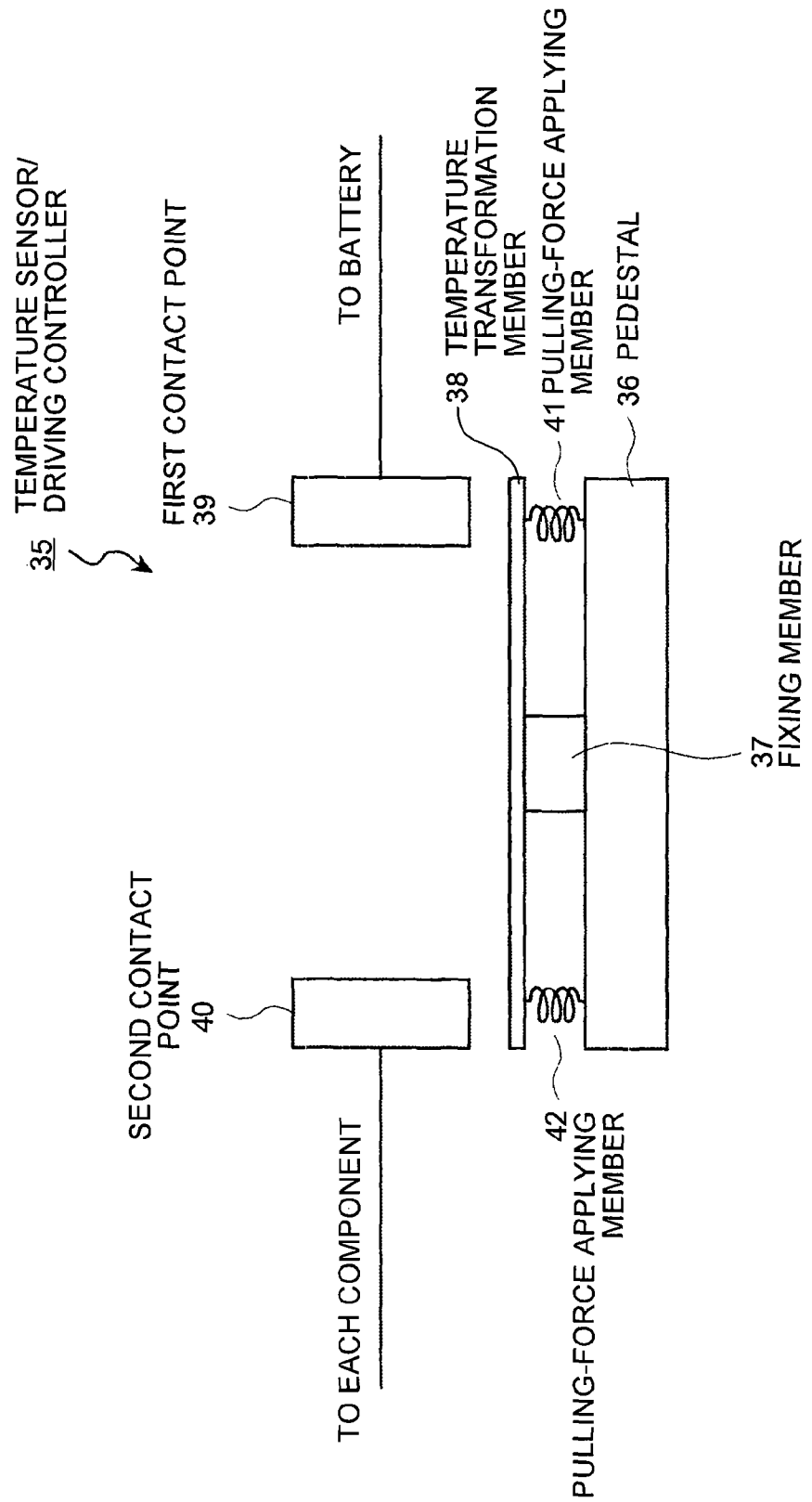
FIG. 5 is a schematic diagram showing a configuration of a temperature sensor/driving controller provided in the capsule endoscope according to a first example of the first embodiment.

A first example of the first embodiment will be explained next. A feature of the first example of the first embodiment is a configuration provided in the capsule endoscope 3 in which the temperature sensor unit 33 and the driving controller 34 are integrally formed. FIG. 5 is a schematic diagram showing a configuration of a temperature sensor/driving controller 35 according to the first example of the first embodiment. Components other than the temperature sensor/driving controller 35 are the same as those of the capsule endoscope 3 according to the first embodiment.

As shown in FIG. 5, the temperature sensor/driving controller 35 includes a temperature transformation member 38 that is arranged in such a manner that the temperature transformation member 38 is fixed to a fixing member 37 arranged on a pedestal 36, a first contact point 39 electrically connected to the battery 100, and a second contact point 40 electrically connected to a component such as the system control circuit 32. In addition, between the pedestal 36 and the temperature transformation member 38, a pulling-force applying members 41 and 42 that apply a pulling force to the temperature transformation member 38 are provided.

The temperature transformation member 38 has a critical point temperature that is the above threshold temperature, and includes shape-memory alloy or shape-memory resin that recovers the memorized shape at a temperature equal to or higher than the critical point temperature. Moreover, the temperature transformation member 38 includes, in a case where the shape-memory resin is provided, a conductive layer on at least a surface facing the first contact point 39 and the second contact point 40 such that electrical connection with the first contact point 39 and the second contact point 40 is established through the conductive layer when the memorized shape is recovered. The pulling-force applying members 41 and 42 are formed with an elastic member such as an elastic spring to apply, to the temperature transformation member 38, a pulling force toward the pedestal 36.

Figure 6A:
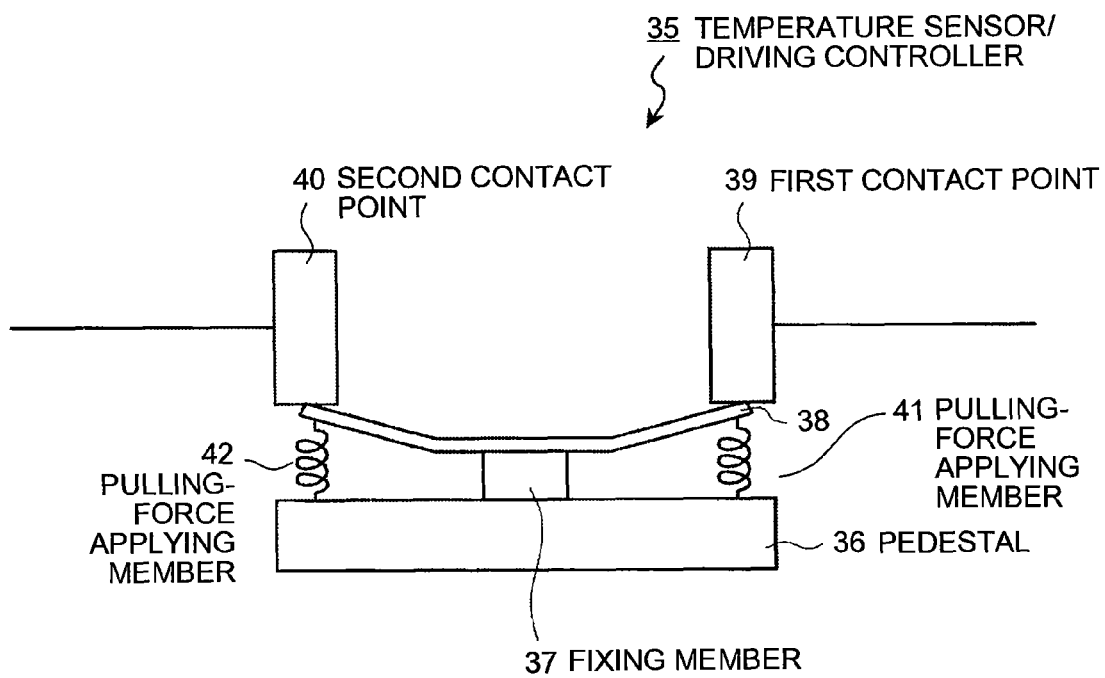
FIG. 6-A is a schematic diagram showing a state of the temperature sensor/driving controller under a temperature higher than a threshold temperature.
Figure 6B:
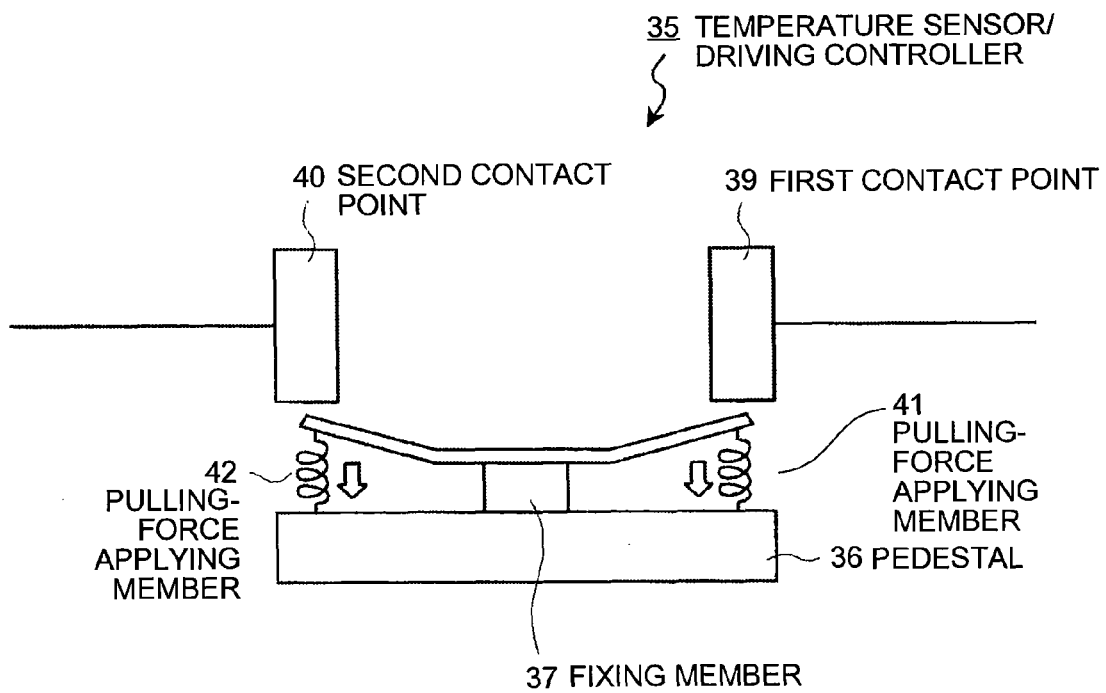

FIG. 6-A is a schematic diagram showing a state of the temperature sensor/driving controller 35 under a temperature higher than the threshold temperature. The temperature transformation member 38 is processed into a U-shape contacting the first contact point 39 and the second contact point 40 at a temperature equal to or higher than the critical point temperature in advance, and then, is shaped into a rod shape as shown in FIG. 5, lowering the temperature below the critical point. Therefore, the temperature transformation member 38 recovers the original shape by being exposed to a temperature equal to or higher than the threshold temperature (=critical point temperature) to take the shape contacting the first contact point 39 and the second contact point 40 as shown in FIG. 6-A. By adopting this configuration, when the capsule endoscope is introduced inside the body of the subject 1 and when temperature of the temperature sensor/driving controller 35 becomes equal to or higher than the threshold temperature, the first contact point 39 and the second contact point 40 are electrically connected. Since the first contact point 39 and the second contact point 40 are electrically connected to the battery 100 and each component in the capsule endoscope respectively, when temperature becomes equal to or higher than the threshold temperature, driving power is supplied to each component in the capsule endoscope from the battery 100, to start driving.

In addition, by providing the pulling force applying members 41 and 42, it is possible to stop the power supply when the temperature becomes below the threshold temperature again after the temperature once becomes equal to or higher than the threshold temperature to start supply of the driving power. In other words, when temperature of the temperature transformation member 38 becomes below the threshold, soft martensitic phase is generated inside the shape-memory alloy (shape-memory resin) that forms the temperature transformation member 38, and therefore, the force applied by the pulling-force applying members 41 and 42 become superior as shown in FIG. 6-B. As a result, the temperature transformation member 38 returns back to the rod shape shown in FIG. 5, and the electrical connection between the first contact point 39 and the second contact point 40 is canceled. Thus, the power supply from the battery 100 is cut to stop driving of each component.

As described above, in the first example of the first embodiment, by providing the temperature transformation member 38 including shape-memory alloy or shape-memory resin having a critical point temperature that is equivalent to the threshold temperature, control of the driving condition according temperature is enabled. In the first embodiment, a configuration without the pulling-force applying members 41 and 42 can be obtained by arranging the shape of the temperature transformation member 38. Specifically, by forming the temperature transformation member 38 such that both ends thereof have more weight than other regions thereof, the temperature transformation member 38 can be configured to be separated from the first contact point 39 and the second contact point 40 at a temperature lower than the threshold, due to the weight at both ends.

A second example of the first embodiment will be explained next. In the second example of the first embodiment, the temperature sensor/driving controller in which the temperature sensor unit 33 and the driving controller 34 are integrally formed is provided in a similar manner as the first example of the first embodiment described above. Moreover, similarly to the first example, components other than the temperature sensor unit 33 and the driving controller 34 are the same as those of the radio in-vivo information acquiring system according to the first embodiment.

FIG. 7 is a schematic diagram showing a configuration of a temperature sensor/driving controller 43 according to the second example of the first embodiment. In FIG. 7, common names and common reference characters are used for parts common with the first example, and specific configurations and effects are also similar to the first example.

The temperature sensor/driving controller 43 includes the pedestal 36, the fixing member 37 that is fixed on the pedestal 36, and a bimetal member 44 that is formed on the fixing member 37. Moreover, the temperature sensor/driving controller 43 includes the first contact point 39 that is electrically connected the battery 100, and the second contact point 40 that is electrically connected to each component in the capsule endoscope.

The bimetal member 44 is formed by attaching a first metal member 45 having a high thermal expansion coefficient and a second metal member 46 having a thermal expansion coefficient lower than that of the first metal member 45 to each other. In the second example of the first embodiment since it is necessary to provide a function of curving the bimetal member 44 such that each end of the bimetal member 44 contacts the first contact point 39 and the second contact point 40 at a temperature equal to or higher than the threshold temperature, the bimetal member 44 has a structure in which the second metal member 46 having lower thermal expansion coefficient is positioned on a side of the first contact point 39 and the second contact point 40.

Figure 8A:
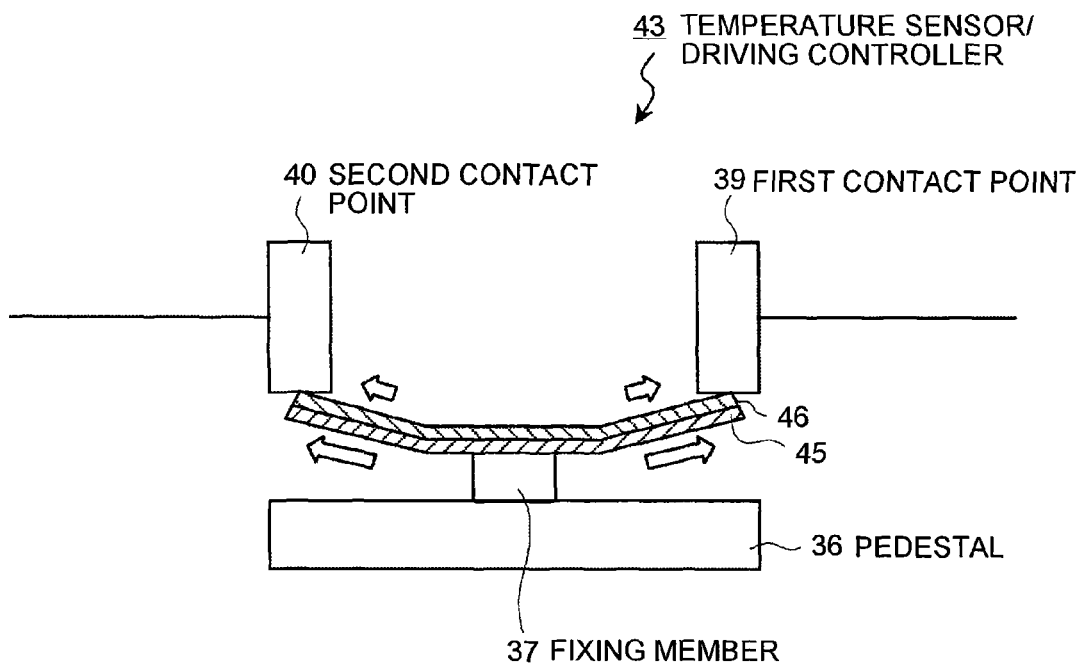
FIG. 8-A is a schematic diagram showing a state of the temperature sensor/driving controller under a temperature higher than a threshold temperature.
Figure 8B:
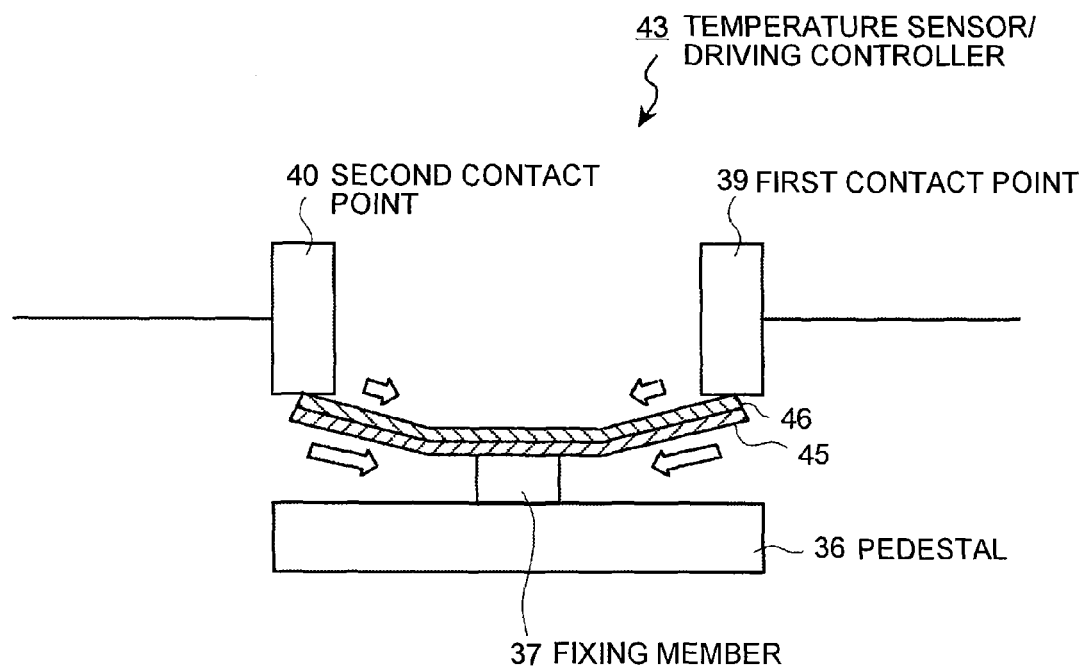

An operation of the temperature sensor/driving controller 43 according to the second example will be explained next. FIG. 8-A is a schematic diagram showing a state of the temperature sensor/driving controller 43 when the bimetal member 44 is heated up to a temperature equal to or higher than the threshold temperature. In the bimetal member 44, while the first metal member 45 has a high thermal expansion coefficient, the second metal member 46 has a low thermal expansion coefficient. Therefore, when the bimetal member 44 is heated, while the volume of the first metal member 45 remarkably expands, the volume of the second metal member 46 does not expand much. Therefore, as shown with arrows in FIG. 8-A, in the bimetal member 44, while a large expansion force in a crosswise direction is generated in the first metal member 45, a small force in the crosswise direction is generated in the second metal member 46.

As a result, the bimetal member 44 changes the shape thereof from the rod shape as shown in FIG. 7 at low temperature to a curved shape having a form convex downward. Being curved, both ends of the bimetal member 44 approach to the first contact point 39 and the second contact point 40 respectively, and when reaching to the threshold temperature, contact to the first contact point 39 and the second contact point 40. Thus, the first contact point 39 and the second contact point 40 are electrically connected, and the driving power is supplied to each component. With this operation of the temperature sensor/driving controller 43, it becomes possible to start supply of the driving power when the temperature of the bimetal member 44 increases to a temperature equal to or higher than the threshold temperature from a low temperature state.

On the other hand, a case in which the bimetal member 44 that has once been heated up is cooled down to a temperature lower than the threshold again is explained with reference to FIG. 8-B. In such a case, in the bimetal member 44, a contraction force is generated such that the first metal member 45 and the second metal member 46 that constitute the bimetal member 44 respectively contract. In this case also, due to the difference in the thermal expansion coefficients, the contraction force generated in the first metal member 45 is smaller than the contraction force generated in the second metal member 46 as shown in FIG. 8-B.

Therefore, the shape of the bimetal member 44 transforms from the curved shape at the increased temperature to have a larger curvature radius, in other words, to a gently curved shape, and finally returns to the rod shape before increasing the temperature. As a result, both ends of the bimetal member 44 separate from the first contact point 39 and the second contact point 40 respectively, the electrical connection between the first contact point 39 and the second contact point 40 is lost, and the power supply to each component is cut. With this operation of the temperature sensor/driving controller 43, it becomes possible to stop the power supply when the temperature of the bimetal member 44 decreases to temperature below the threshold temperature from a high temperature state.

The first and second examples of the first embodiment have been explained as above, and in either of the examples, a mechanism functioning as the temperature sensor unit 33 and the driving controller 34 can be realized with a simple configuration. In other words, because a switching mechanism is realized with a member that physically changes the shape thereof corresponding to a temperature change in each of the first and the second examples, the temperature sensor unit 33 and the driving controller 34 can be configured without a complicated electric circuit and the like. Furthermore, by adopting a member that physically changes the shape thereof corresponding to a temperature change, the temperature sensor unit 33 and the driving controller 34 can be configured to operate without power, thereby contributing to lowering power consumption of the capsule endoscope 3.

Second Embodiment

A radio in-vivo information acquiring system according to a second embodiment will be explained next. The radio in-vivo information acquiring system according to the second embodiment has such a configuration that a temperature sensor and a driving controller are provided in a capsule endoscope to be a body-insertable apparatus with a low heat conductive member that covers at least the temperature sensor.

Figure 9:
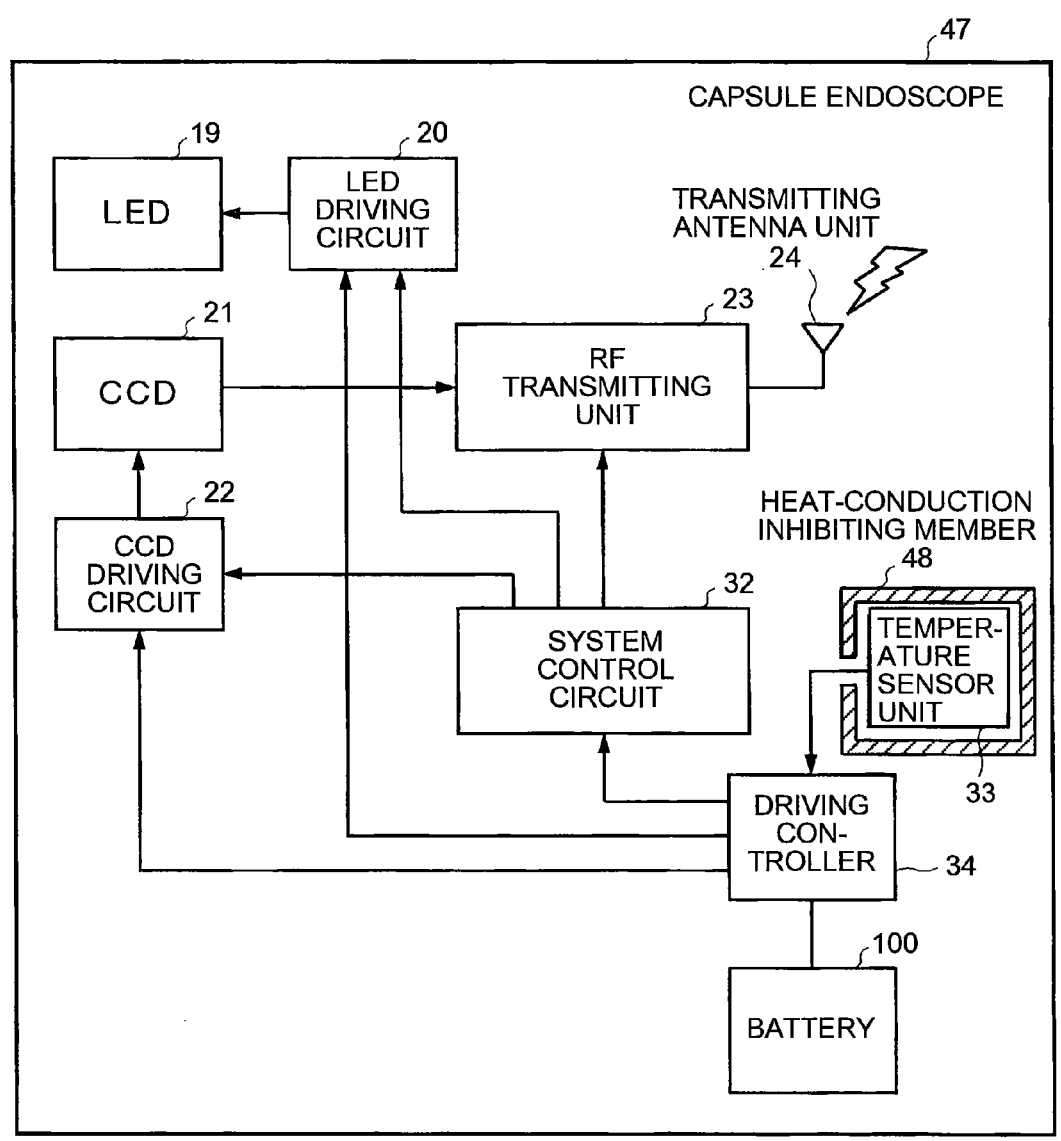
FIG. 9 is a block diagram schematically showing a configuration of a capsule endoscope constituting a radio in-vivo information acquiring system according to a second embodiment.

FIG. 9 is a block diagram schematically showing a configuration of a capsule endoscope 47 constituting the radio in-vivo information acquiring system according to the second embodiment. In the second embodiment, the receiving device, the display device, and the portable recording medium that are other components of the radio in-vivo information acquiring system have the same configuration and the same function as those of the first embodiment unless otherwise specified below.

The capsule endoscope 47 according to the second embodiment includes the LED 19 to illuminate inside the subject, the LED driving circuit 20 that controls driving of the LED 19, the CCD 21 that performs an imaging operation, the CCD driving circuit 22 that controls driving of the CCD 21, the RF transmitting unit 23 that performs modulation and the like on image data acquired by the CCD, the transmitting antenna unit 24 that performs transmission operation, and the battery 100.

Moreover, the capsule endoscope 47 includes the system control circuit 32 that controls the driving condition of the LED driving circuit 20, the CCD driving circuit 22, and the RF transmitting unit 23. Furthermore, the driving controller 34 is provided that controls power supply from the battery 100 based on the temperature sensor unit 33 covered with a heat-conduction inhibiting member 48, and on temperature data output from the temperature sensor unit 33.

The heat-conduction inhibiting member 48 is to inhibit conduction of heat in ambient environment to the temperature sensor unit 33. Specifically, the heat-conduction inhibiting member 48 is not to prevent conduction of heat in the ambient environment but is formed with a member that conducts heat at some rate. By providing the heat-conduction inhibiting member 48, the temperature sensor unit 33 detects influence of a temperature change in the ambient environment, for example, the temperature change occurring when the capsule endoscope is introduced inside the body of the subject 1, after a predetermined time has elapsed. In other words, by being covered with the heat-conduction inhibiting member 48, temperature detected by the temperature sensor unit 33 maintains a value lower than the threshold temperature immediately after the capsule endoscope 47 is introduced inside the body of the subject 1. As time elapses, heat is gradually conducted through the heat-conduction inhibiting member 48 to the temperature sensor unit 33. Thus, after some time elapses, the temperature becomes a value equal to or higher than the threshold temperature.

Advantages obtained by providing this configuration that the temperature sensor unit 33 is covered with the heat-conduction inhibiting member 48 will be explained. Since usual capsule endoscopes have a compact shape and constituent parts having high thermal conductivity are used, for example, when introduced inside the body of the subject 1, temperature of the capsule endoscope becomes equivalent to body temperature of the subject 1 immediately after introduction into the subject 1. Therefore, if the driving condition is controlled by providing a temperature sensor unit in the capsule endoscope while setting a temperature equivalent to or a little lower than the body temperature as the threshold temperature, the capsule endoscope is actuated immediately after the capsule endoscope is introduced into the body of the subject 1, thereby quickly starting imaging and the like.

However, when image data is to be acquired from an organ such as a small intestine located at a position that requires a certain amount of time to be reached after the capsule endoscope is introduced into the body of the subject 1, image data of portions located before the imaging target portion is not necessary. As described above, when image data of a specific portion is required, it is demanded to prevent the driving power from being supplied to each component in the capsule endoscope until the capsule endoscope reaches to the specific portion.

Based on the demand, in the second embodiment, it is configured to require a certain amount of time until temperature detected by the temperature sensor unit 33 reaches to a temperature equal to or higher than the threshold temperature by covering the temperature sensor unit 33 with the heat-conduction inhibiting member 48, thereby preventing each component provided in the capsule endoscope 47 from starting driving immediately after introduction into the body of the subject 1. Further, by arranging the configuration of the heat-conduction inhibiting member 48, time required until the temperature reaches the threshold temperature is adjusted. Thus, driving can be started only after reaching a predetermined tested portion for which image data is necessary.

By adopting this configuration, in the capsule endoscope 47, it becomes possible to prevent acquisition of unnecessary image data not only outside the body of the subject 1 but also inside the body of the subject 1. Therefore, it is possible to prevent acquisition of unnecessary image data, and to suppress waste of driving power, further effectively.

While in the configuration shown in FIG. 9, the heat-conduction inhibiting member 48 only covers the temperature sensor unit 33, it is not limited to this configuration, and for example, a capsule casing in which each component of the capsule endoscope 47 is housed can be formed with a material having a heat-conduction inhibiting function. Alternatively, the capsule casing can be formed with a regular material and the exterior of the capsule casing can be covered with a material having the heat-conduction inhibiting function.

Moreover, it can be configured so that the portion covered with the heat-conduction inhibiting member 48 corresponds a part of the temperature sensor unit 33. In other words, as long as heat conduction from an ambient environment is inhibited in a portion actually detecting temperature, for example, it can be configured to cover only the temperature transformation member 38 included in the configuration shown in FIG. 5 with the heat-conduction inhibiting member 48.

For a material constituting the heat-conduction inhibiting member 48, mainly two types of materials can be applied. First, a material having a low thermal conductivity such as Styrofoam can be used to form the heat-conduction inhibiting member 48. By using this material, an amount of heat conducted to the temperature sensor unit 33 per unit time is lowered, thereby configuring such that a certain amount of time is required until the temperature sensor unit 33 detects temperature of the ambient environment.

As another example, a material that is maintained at a temperature lower than the ambient temperature can be used for the heat-conduction inhibiting member 48. That is, in a case where the material maintained at a temperature lower than the ambient temperature is used for the heat-conduction inhibiting member 48, when heat is to be conducted to the temperature sensor unit 33, the conducted heat is used to increase the temperature of the heat-conduction inhibiting member 48, and temperature of the temperature sensor unit 33 starts rising after the temperature of the heat-conduction inhibiting member 48 reaches a predetermined temperature. Therefore, even when the ambient temperature changes to a temperature equal to or higher than the threshold temperature, temperature sensor unit 33 detects the temperature equal to or higher than the threshold after a predetermined time has elapsed from the change. Thus, the material maintained at a temperature lower than the ambient temperature can function as the heat-conduction inhibiting member 48.

A specific example of using the material maintained at lower temperature is used as the heat-conduction inhibiting member 48 includes such a configuration that when introducing into the body of the subject 1, the capsule endoscope is introduced, for example, with tap water of about 20° C. In this case, the tap water to be introduced with has a temperature lower than at least the ambient temperature of the capsule endoscope inside the subject 1, and by the tap water surrounding the capsule endoscope, heat conduction to the capsule endoscope from the ambient environment is inhibited, thereby preventing acquisition of image data by the capsule endoscope and transmission of the acquired image data by radio communication from being started before a predetermined time elapses from when the capsule endoscope is introduced inside the body of the subject 1.

While the present invention has been explained with the first and the second embodiments above, the present invention is not limited to the above, and those skilled in the art can think of various embodiments, modification, and application. For example, in the first and the second embodiments, the capsule endoscope includes the LED, the CCD, and the like to acquire images inside the subject 1. However, the body-insertable apparatus to be introduced into the body of a subject is not limited to this configuration, and for example, can be configured to acquire other in-vivo information such as temperature information and pH information. Moreover, the body-insertable apparatus can include an oscillator to acquire ultrasound images inside the subject 1. Furthermore, the body-insertable apparatus can be configured to acquire a plurality of types of information among the in-vivo information.

In addition to the configuration in which only reception of the radio signal output from the capsule endoscope is performed, the receiving device 2 can be configured to transmit a power supply signal to supply power to the capsule endoscope so that driving power is regenerated from the power supply signal received at the capsule endoscope. Moreover, a storing unit can be provided in the capsule endoscope, and information can be extracted from the storing unit after the capsule endoscope is discharged from the body of the subject 1.

Furthermore, the threshold temperature is not necessarily set to a temperature lower than body temperature of the subject 1. For example, when the system is developed for the purpose of imaging a specific affected portion present in the body of the subject 1, and if the specific affected portion has higher temperature than other areas in the subject 1, temperature corresponding to such a temperature can be applicable to the threshold temperature.

Furthermore, in the first and the second embodiments, it is configured such that the driving power is supplied to each component such as the LED 19 through the driving controller 34. However, it can be configured such that the power is directly supplied to each component. Moreover, a component controlled by the driving controller can be a part of the components in the capsule endoscope, such as the RF transmitting unit 23 only. Moreover, while in the first and the second embodiments, the driving controller is configured to stop the driving of each component both before the capsule endoscope is introduced into the body of the subject and after being discharged from the subject, the driving controller can be configured to perform a stop control only either of the cases. This is because even if the stop control is performed in only either one of the cases, it is still possible to prevent acquisition of unnecessary image data and to lower the power consumption compare to the conventional technologies.

Third Embodiment

Figure 10:
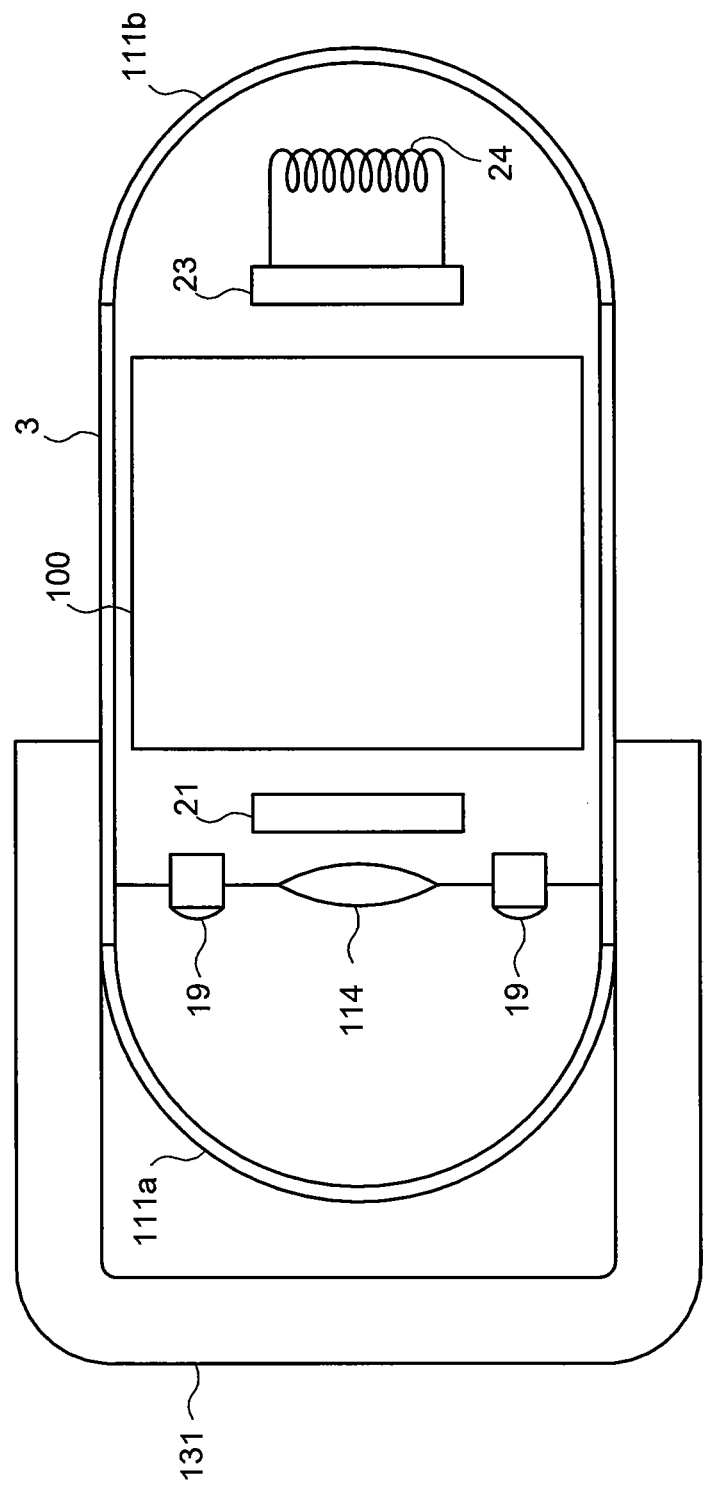
FIG. 10 is a cross-section showing a schematic configuration of the capsule endoscope shown in FIG. 1.

FIG. 10 is a cross-section showing a schematic configuration of the capsule endoscope shown in FIG. 1. In the drawings hereafter, like reference characters denote like parts as those shown in FIG. 1 for the convenience of explanation.

As shown in the cross-section of FIG. 10, for example, the capsule endoscope 3 is formed with an elliptic capsule having a spherical shape at each end, and includes a transparent dome 11*a* that is provided in a front side of the capsule endoscope, an imaging mechanism as an information acquiring unit or an imaging unit that acquires image data by imaging body cavities, and a radio communication mechanism as a radio unit that transmits various information including this image data. A dome protection cap 131 is mounted so as to cover a dome 111*a* on the capsule endoscope 3 before being introduced into the body of a subject. The cap 131 is detachably provided to the dome 111*a*, and when the examinee introduces the capsule endoscope 3 inside the subject by swallowing, this cap 131 is removed from the capsule endoscope 3, thereby enabling imaging inside body cavities.

The imaging mechanism includes the illuminating device 19 such as a light emitting device (LED) to illuminate inside the body cavities of the subject 1, the imaging device 21 such as a charge-coupled device (CCD) and a CMOS imaging camera that acquires images, which are reflected light, inside the body cavities, and an optical system part 114 that causes the imaging device 21 to form images. The illuminating device 19 lights internal portion of the body cavities through the dome 111*a* at the front side. The imaging device 21 captures the reflected light to acquire images of examined areas inside the body cavities.

The radio communication mechanism includes a radio unit (RF transmitting unit) 23 that modulates acquired image signals into RF signals to transmit, and the transmitting antenna (transmitting antenna unit) 24 that emits radio waves of the RF signals to the outside of the body of the subject 1. The radio communication mechanism is provided inside a dome 111*b* at a rear side. The capsule endoscope 3 includes the power source device (battery) 100 such as a silver oxide battery that supplies power to electric parts provided therein, such as the LED 19, the CCD 21, the radio device 23, and the transmitting antenna 24. Further, for example, if a receiver and a receiving antenna are provided in the capsule endoscope 3, driving of the LED, the CCD, and the like described above can be controlled based on various control signals from the external device 2*b*.

Figure 11:
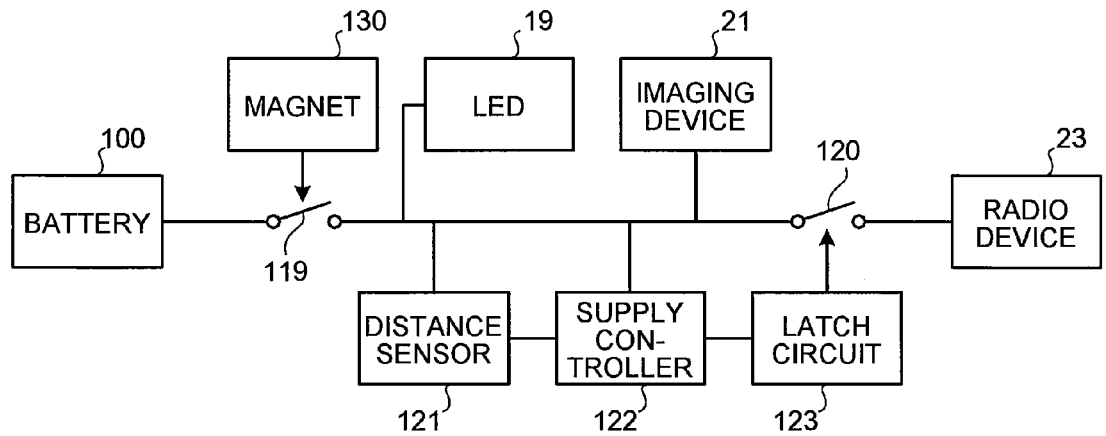
FIG. 11 is a block diagram showing a configuration according to a third embodiment of an electric system in the capsule endoscope shown in FIG. 1.

FIG. 11 is a configuration diagram showing a configuration of an electrical system in the capsule endoscope according to the third embodiment of the present invention. A usual body-insertable apparatus 3 is equipped with the illuminating device (illuminating unit) 19 constituted by an LED, the imaging device 21 constituted by an imaging camera, the radio device 23 that communicates radio waves, the power source device 100 constituted by a battery that supplies power to these electric components, and the lead switch 19 provided between the power source device 100 and each of the electric components. A lead switch 119 is switched on and off according to restriction and release by a magnetic member (magnet) 130 provided in a package holding the capsule endoscope 3 before use.

In this configuration, the lead switch 119 is configured to be turned on and off in response to, for example, separation and approach of the magnet 130 respectively. The lead switch 119 in an initial state of being held in the package is turned into an on state upon separation of the magnet 130 provided in the package, and once turned into the on sate, the lead switch 119 maintains this state. Therefore, power is to be constantly supplied to each of the electric components from the battery 100. The lead switch 119 can also be configured to be turned on and off in response to approach and separation of the magnet 130 respectively.

On the other hand, in the capsule endoscope 3 shown in FIG. 11, the radio device 23 is connected to the battery 100 through the lead switch 119 and a subswitch 120, and a distance sensor 121 as a detector that detects a distance between the imaging subject and the capsule endoscope 3, a supply controller 122 as a supply control unit that controls on and off of the subswitch 120, and a latch circuit 123 are provided. Specifically, in the present embodiment, when only the lead switch 119 is in the on state (the subswitch 120 is in the off state), the radio device 23 is not supplied with power. Therefore, the radio device 23 is not turned on and cannot transmit image data acquired by the imaging device 21.

The distance sensor 121 and the supply controller 122 are connected so as to be supplied with power from the battery 100 when the lead switch 119 is turned into the on state, and when the distance sensor 121 detects the distance between the imaging subject and the capsule endoscope 3, the supply controller 122 controls the subswitch 120 to be turned into the on state based on the detected distance.

Namely, the distance sensor 121 is a general sensor used for distance detection, and is configured to emit, for example, infrared ray through the dome 111*a* when the lead switch 119 is turned on, and to detect the distance between the imaging subject, which lies in a path of the infrared ray, and the capsule endoscope 3 based on an arriving time of the infrared ray reflected from the imaging subject.

The supply controller 122 is connected so as to be supplied with power from the battery 100 when the lead switch 119 is turned on. When the distance between the imaging subject and the capsule endoscope 3 is detected by the distance sensor 121, and when the detected distance is less than a threshold (information indicating that the capsule endoscope 3 has been introduced inside a body cavity), the supply controller 121 determines that the capsule endoscope 3 has been swallowed into the body of the subject, outputs a control signal to control operation of the latch circuit 123, thereby turning on the subswitch 120.

The latch circuit 123 is constituted by, for example, a D-type flip flop circuit, and once the control signal is input from the supply controller 122, causes the subswitch 120 to be turned on. The on state is thereafter maintained to continue the power supply to the radio device 23.

Figure 12:
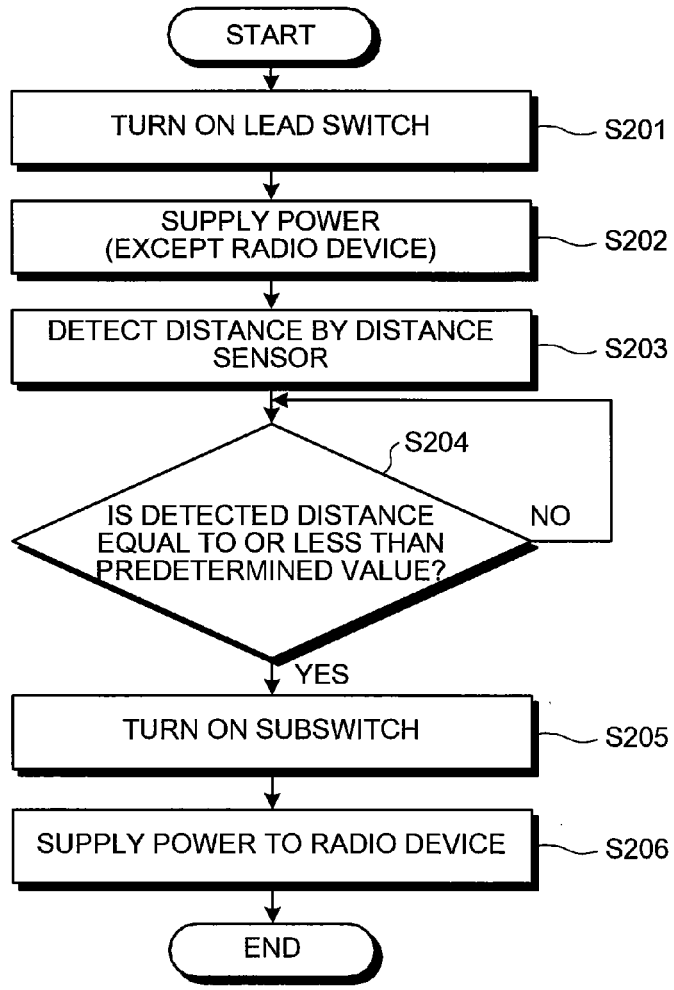
FIG. 12 is a flowchart for explaining power supply operation of the capsule endoscope shown in FIG. 11.

A power supply operation of the radio in-vivo information acquiring system will be explained next with reference to a flowchart shown in FIG. 12. As shown in FIG. 12, upon being taken out of the package, the capsule endoscope 3 is released from influence of the magnetic force of the magnet 130, and the lead switch 119 is turned into the on state (step 201). When the lead switch 119 is turned on, each electric component (the LED 19, the imaging device 21, the distance sensor 121, and the supply controller 122 in this example) except the radio device 23 is supplied with power (step S202). The imaging device 21 starts imaging and the distance sensor 121 detects the distance to the imaging subject that is present in front, to output the distance data to the supply controller 122 (step S203).

Upon receiving this distance data, the supply controller 122 determines whether the detected distance is less than the threshold (step S204). When the distance is less than the threshold, the supply controller 122 determines that the capsule endoscope 3 has entered inside a body cavity, to control the subswitch 120 to be in on state (step S205). Thus, power is supplied to the radio device 23 from the battery 100 (step S206). With the power supply, the radio device 23 is turned on and transmits image data inside the body cavity acquired by imaging by the imaging device 21 while the LED 19 illuminates.

As described above, in the present embodiment, it is determined whether the capsule endoscope is positioned inside a body cavity based on distance data detected by the distance sensor, to determine whether to supply power to the radio device. Therefore, timing of power supply to the radio device can be adjusted to be after the capsule endoscope is certainly introduced inside the body of the subject, thereby accurately performing collection and transmission of images inside the subject while lowering the power consumption.

In the body-insertable apparatus according to the third embodiment described above, it is conceivable that the subswitch is turned into the on state immediately after being introduced into the mouth of a subject. It can be demanded to supply power to the radio device when it is completely introduced inside an organ of an examined target, not immediately after being swallowed.

Figure 13:
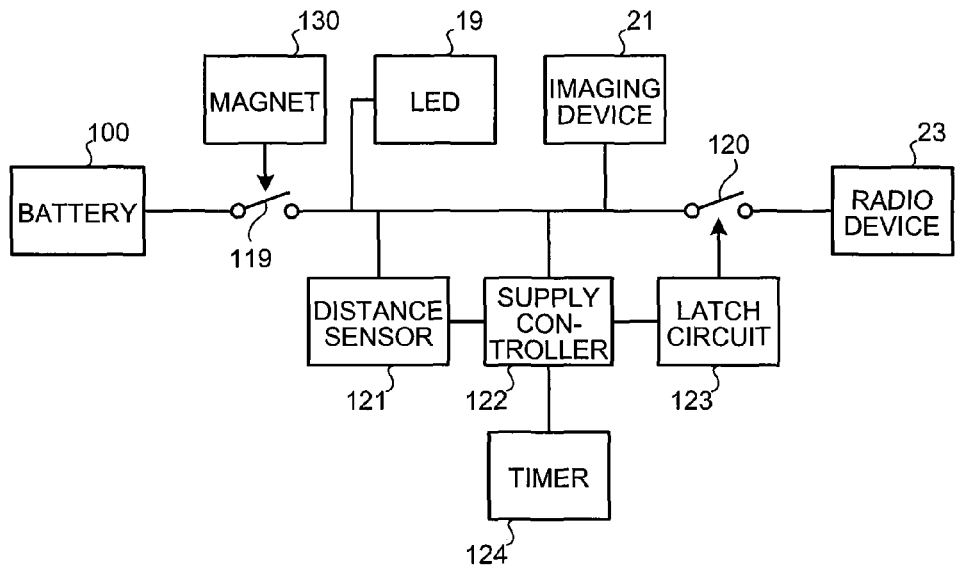
FIG. 13 is a block diagram showing another configuration according to a third embodiment of the electric system in the capsule endoscope shown in FIG. 1.

FIG. 13 is a block diagram showing another configuration of the third embodiment contrived in response to such demand. In the configuration shown in FIG. 13, difference from that shown in FIG. 11 is that a timer 124 is connected to the supply controller 122 so that power is supplied to the radio device 23 to perform transmission of the image data when a predetermined time has elapsed after the distance to the imaging subject becomes less than the threshold.

For example, when transmission of the image data is to be started after the capsule endoscope is introduced inside the stomach, a predetermined time required for the capsule endoscope 3 to reach the stomach after the detected distance becomes less than the threshold is set in the timer 124 in advance. The supply controller 122 starts the timer 124 when the acquired distance becomes less than the threshold, and controls the latch circuit 123 when the predetermined time has elapsed to turn on the subswitch 120. Thus, the radio device 23 is supplied with power from the battery 100 when the capsule endoscope 3 is certainly introduced inside the stomach of the examined target, to transmit image data inside the stomach acquired by imaging by the imaging device 21 while the LED 19 illuminates, to the outside.

As described above, in the present embodiment, the power supply to the radio device is started when the capsule endoscope has been introduced inside the examined target, thereby accurately performing collection and transmission of images of an examined target inside a body of a subject while further lowering the power consumption.

Fourth Embodiment

The distance sensor used in the third embodiment is complex in structure and costly, therefore, application thereof to the capsule endoscope is considered to be difficult. In the present embodiment, a body-insertable apparatus is provided in which power supply to the radio device 23 is executed, detecting an amount of light in front of the dome 111a with a light amount sensor, to determine distance to the imaging subject based on correlation between light amount and distance.

Figure 14:
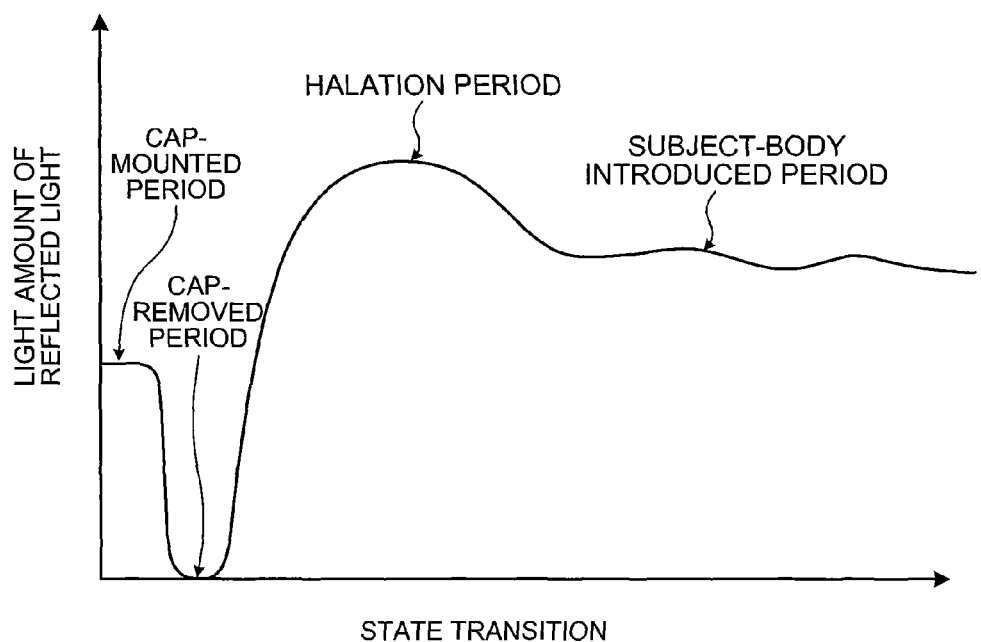
FIG. 14 is a relational diagram showing a relationship between a light amount of a reflected light and a position (distance) of each imaging subject.

In other words, as shown in an amount of reflected light and a position of an imaging subject shown in FIG. 14, there is a correlation between the amount of reflected light and the position of each imaging subject such that an amount of reflected light from the imaging subject changes at the time when the cap is installed (distance to an inner wall of the cap), at the time when the cap is removed (distance to an imaging subject outside the body of the subject), at the time of introducing into the body of the subject (distance to the inside of a body cavity), and at the time when an inner wall of the dome 111a is fogged (halation) due to temperature difference outside and inside the body of the subject (distance to the inner wall of the dome). Based on the correlation between the light amount and the distance to the imaging subject, distance to an imaging subject can be detected.

Figure 15:
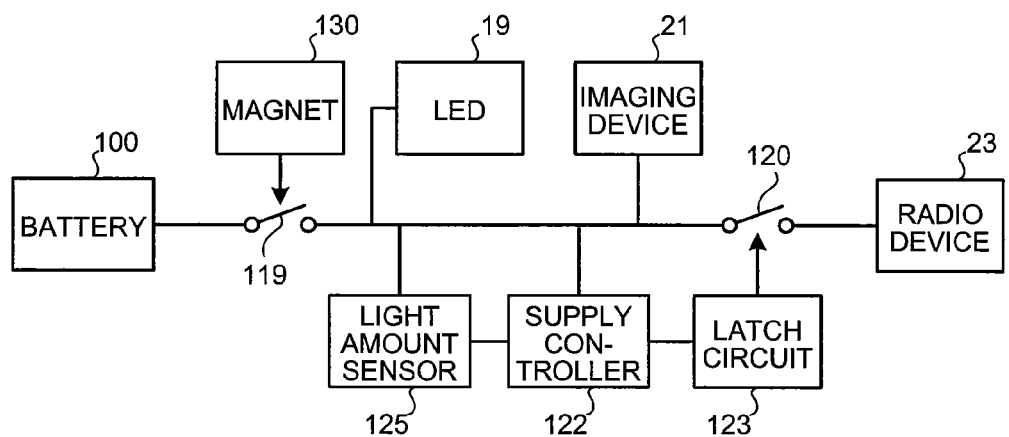
FIG. 15 is a block diagram showing a configuration according to a fourth embodiment of an electric system in the radio in-vivo information acquiring system shown in FIG. 1.

FIG. 15 is a configuration diagram showing a configuration of an electrical system of the capsule endoscope according to the fourth embodiment of the present invention. In the present embodiment, a light amount sensor 125 is provided to detect an amount of reflected light from an imaging subject illuminated by the LED 19. When the capsule endoscope is outside a body of a subject, the light from the LED 19 is difficult to reach the imaging subject, therefore, the light amount to be detected is small, and when the capsule endoscope is inside a body of a subject, the imaging subject of a body cavity is closely positioned thereto, and the light amount to be detected becomes large.

In the present embodiment, the correlation between the light amount and the distance shown in FIG. 14 is set in advance in the supply controller 122 connected to this light amount sensor 125. Based on this correlation, the supply controller 122 detects the distance to an imaging subject corresponding to the light amount input thereto. When the distance to an imaging subject inside and outside the body of the subject 1 becomes less than the threshold, the supply controller 122 determines that the capsule endoscope 3 has been introduced inside the body of the subject, and controls the latch circuit 123 to control operation of the subswitch 120 to be in the on state.

Thus, in the present embodiment, a distance to an imaging subject is detected based on the correlation between the light amount and the distance, and whether the capsule endoscope is located inside a body cavity is detected based on the distance data detected, to determine whether to supply power to the radio device. Therefore, power supply timing to the radio device can be controlled to be after the capsule endoscope is certainly introduced inside the body of a subject, thereby accurately performing collection and transmission of images inside the subject while lowering the power consumption and manufacturing the capsule endoscope with a simple configuration at low cost.

Moreover, in the present embodiment, for example, even if the inner wall of the dome 111a is fogged (halation) due to temperature difference outside and inside the body of the subject, the distance to the inner wall of the dome can be detected based on an amount of the reflected light. Therefore, it is possible to easily detect whether the capsule endoscope is located inside a body cavity.

Fifth Embodiment

Figure 16:
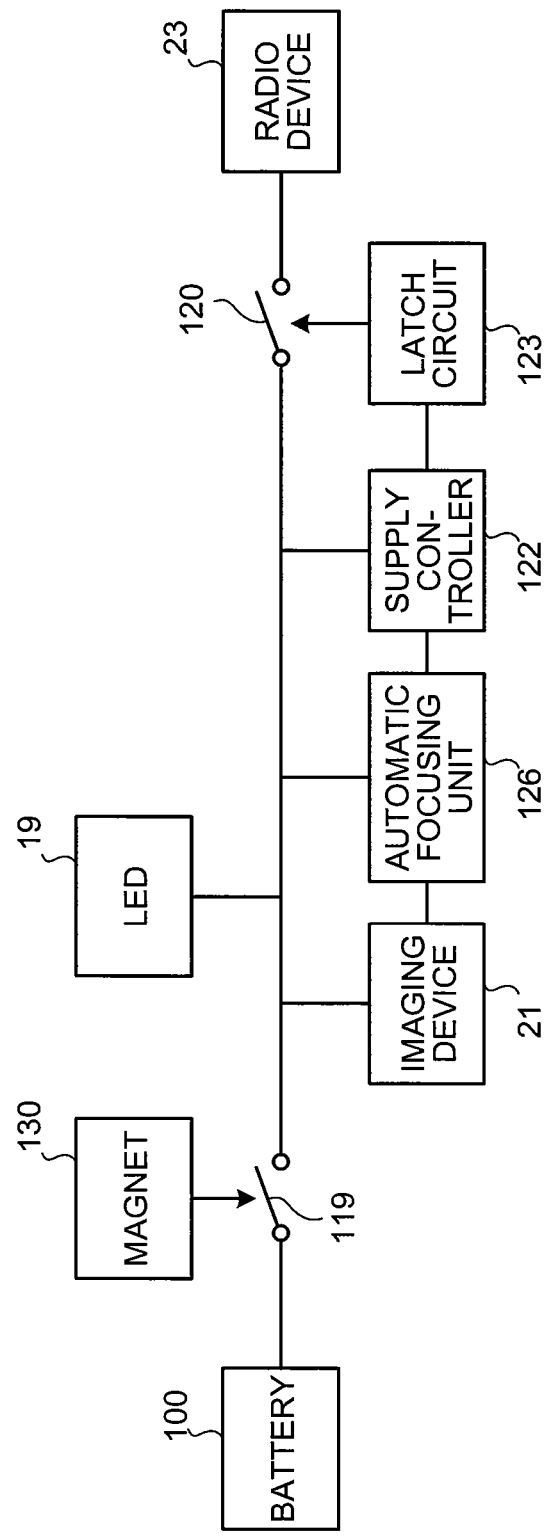
FIG. 16 is a block diagram showing a configuration according to a fifth embodiment of an electric system in the radio in-vivo information acquiring system shown in FIG. 1.

FIG. 16 is a configuration diagram showing a configuration of an electrical system a capsule endoscope according to a fifth embodiment of the present invention. In the present embodiment, it is assumed that the capsule endoscope 3 has an automatic focusing function that controls automatic focus operation. Specifically, in the present embodiment, an automatic focusing unit 126 is connected to the imaging device 21, and image data acquired by the imaging device 21 is output to the automatic focusing unit 126. The automatic focusing unit 126 controls an automatic focus operation based on the image data output from the imaging device 21, and causes the optical system part 114 (see FIG. 10) to shift the position thereof, to obtain correct focus.

The supply controller 122 detects a distance to an imaging subject based on a shift amount of this lens. Furthermore, the supply controller 122 determines whether the detected distance is less than the threshold. When the distance is less than the threshold, the supply controller 122 determines that the capsule endoscope 3 has entered inside a body cavity, and controls the subswitch 120 to be in the on state. Thus, power is supplied to the radio device 23 from the battery 100 to turn on the radio device 23.

In focusing by the automatic focusing unit 126, an optimal focus position is acquired based on sharpness of edge (for example, a slope of the edge at transition from a black image to a white image) in an image, and in the present embodiment, the distance to an imaging subject is detected based on an amount for which the lens is shifted until the optimal focus point is obtained. In this case, a position of the lens to be a reference at an initial state is necessary to be prescribed, and for example, a distance at a focus point of the lens obtained by the automatic focusing unit 126 at when the imaging device 21 acquires an image of an inner wall of the cap in a state in which the cap 131 shown in FIG. 2 is put on the capsule endoscope 3 can be set as the reference distance.

Thus, in the present embodiment, a distance to an imaging subject is detected based on the shift amount of a lens at the time of focusing by the automatic focusing function, and whether the capsule endoscope is located inside a body cavity is detected, to determine whether to supply power to the radio device. Therefore, power supply timing to the radio device can be controlled to be after the capsule endoscope is certainly introduced inside the body of a subject, thereby accurately performing collection and transmission of images inside the subject while lowering the power consumption.

Moreover, also in the fourth and the fifth embodiments, the timer shown in FIG. 13 can be provided to obtain such a configuration that power is supplied to the radio device after the capsule endoscope is certainly introduced inside an organ of an inspection subject.

Sixth Embodiment

First, a radio in-vivo info acquiring system according to a sixth embodiment will be explained. The radio in-vivo information acquiring system according to the sixth embodiment is provided with a driving condition controller that controls a driving condition of each component of a capsule endoscope with a photoelectric converter of which intensity of dark current is temperature dependent, applying temperature difference outside and inside the body of the subject to prevent actuation of the capsule endoscope outside the body of a subject.

Figure 17:
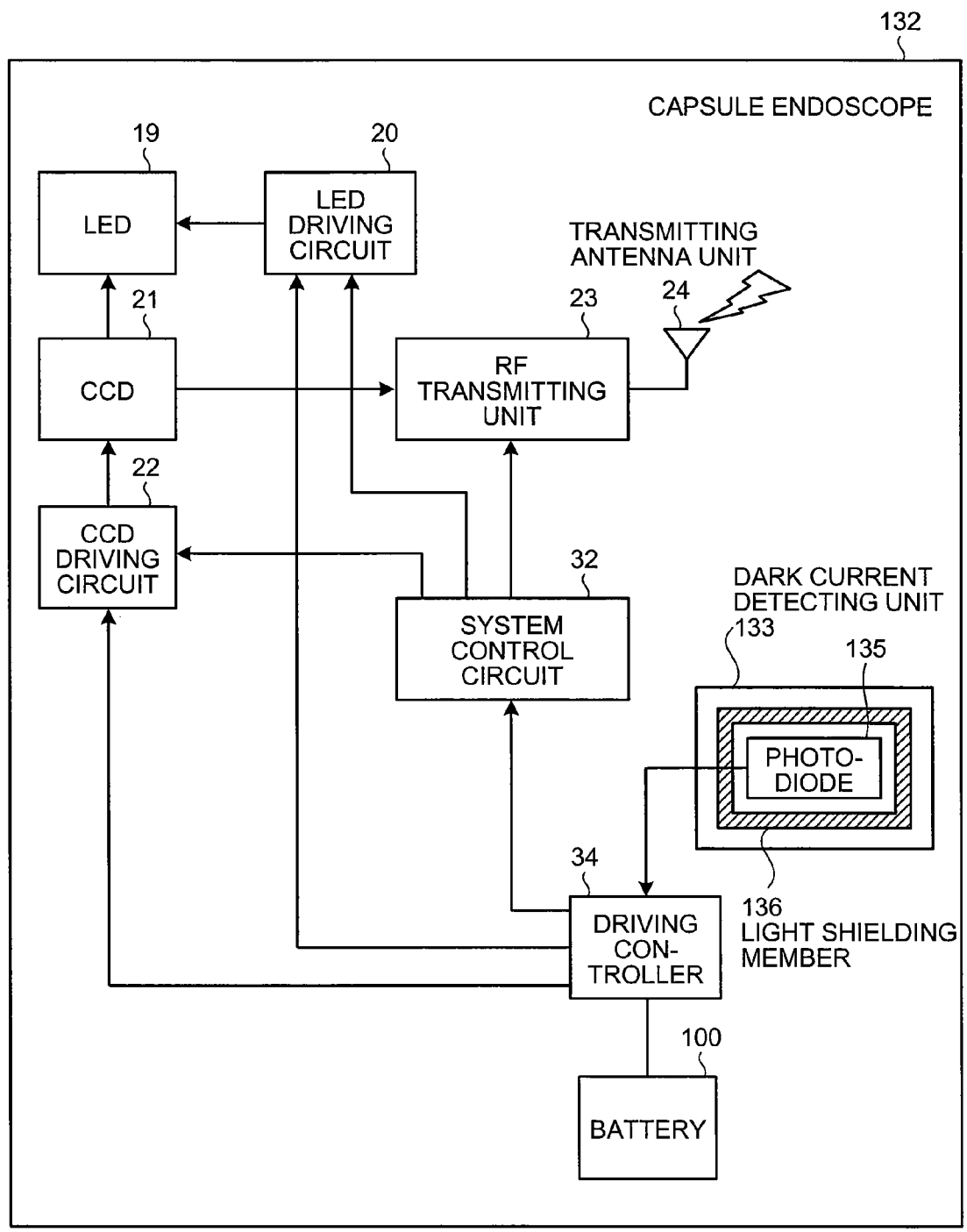
FIG. 17 is a block diagram schematically showing a configuration of a capsule endoscope constituting a radio in-vivo information acquiring system according to a sixth embodiment.

Next, the capsule endoscope 132 will be explained. FIG. 17 is a block diagram schematically showing a configuration of the capsule endoscope 132. As shown in FIG. 17, a capsule endoscope 132 includes the LED 19 as an illuminating unit to illuminate an imaging area when imaging inside the body of the subject, the LED driving circuit 20 that controls a driving condition of the LED 19, and the CCD 21 as a photoelectric converter or an imaging unit that generates image data by imaging a reflected optical image from the area illuminated by the LED 19. Furthermore, the capsule endoscope 132 includes the CCD driving circuit 22 that controls a driving condition of the CCD 21, the RF transmitting unit 23 that modulates the image data acquired by the CCD 21 to generate an RF signal, the transmitting antenna unit 24 as a radio communication unit that transmits the RF signal output from the RF transmitting unit 23, the LED driving circuit 20, and the system control circuit 32 as an operation controller that controls operation of the CCD driving circuit 22 and the RF transmitting unit 23.

With this configuration, the capsule endoscope 132 acquires, by the CCD 21, image information of an inspected portion illuminated by the LED 19 while introduced inside the body of the subject 1. The acquired image information is converted into the RF signal by the RF transmitting unit 23, and then, transmitted to the outside through the transmitting antenna unit 24.

Moreover, the capsule endoscope 132 includes the battery 100 as a power source to drive components inside the capsule endoscope 132 such as the LED driving circuit 20, the CCD driving circuit 22, and the RF transmitting unit 23 as function executing units that executes each predetermined function. The system control circuit 32 controls operating conditions of the LED driving circuit 20, the CCD driving circuit 22, the RF transmitting unit, and the like, more specifically, an operation of the function executing unit such as an illuminating period of the LED 19, a frame rate of the CCD 21, transmission timing of the RF signal or the like based on a predetermined information. The capsule endoscope 132 further includes a dark current detecting unit 133 and a driving controller 34 serving as a driving control unit that controls driving condition of the LED driving circuit 20, the CCD driving circuit 22, the system control circuit 32, and the like based on dark current detected by the dark current detecting unit 133. The driving controller 34 also has a function of distributing driving power supplied by the battery 100 to each component such as the LED driving circuit 20, the CCD driving circuit 22, and the system control circuit 32 serving as the function executing unit. The dark current detecting unit 133 includes a photodiode 135 and a light shielding member 136 that is formed to cover at least a light receiving surface of the photodiode 135.

Driving control performed by the dark current detecting unit 133 and the driving controller 34 that performs driving control on each component as the function executing unit in the capsule endoscope 132 will be explained next. As described above, the dark current detecting unit 133 includes the photodiode 135 and the light shielding member 136, and is configured to output intensity of dark current generated in the photodiode 135 to the driving controller 34. First, the dark current, which is one of electrical characteristics of the photodiode, will be briefly explained.

Figure 18:
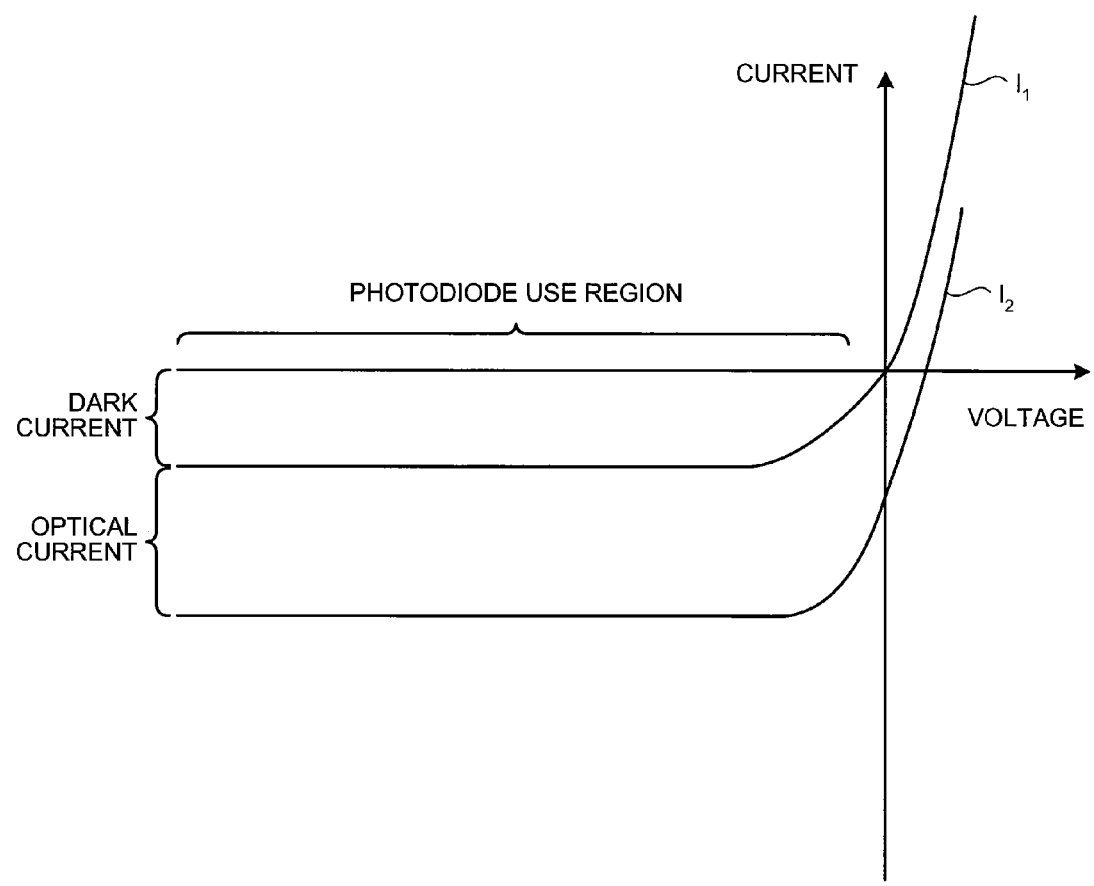
FIG. 18 is a schematic graph for explaining an electrical characteristic of a photodiode.

FIG. 18 is a schematic graph for explaining current flowing through the photodiode. As a specific structure of photodiodes, a structure having a PN junction similarly to a regular diode, and a so-called PIN structure that is used while applying reverse current to a semiconductor member having the PN junction, and the like are known. With either of the structures, basic electrical characteristics are the same as that of diodes, and the photodiodes are used under a condition in which the reverse current is applied to such a structure.

In FIG. 18, a curve $l_1$ shows a current-voltage characteristic of the photodiode when light is not irradiated, and a curve $l_2$ shows a current-voltage characteristic of the photodiode when light is irradiated. As is evident from the curves $l_1$ and $l_2$, in the photodiode used by applying reverse current, current flowing in a reverse direction increases due to light irradiation. The increased amount of the current is called optical current, and based on an amount of the optical current, detection of intensity of irradiated light and the like are possible.

On the other hand, even when no light is irradiated at all, as the curve $l_1$ shows, in a region ("photodiode use region" in FIG. 18) in which the reverse current is applied, current having certain intensity exists. Such current is called dark current, when the photodiode is used as the photoelectric converter, current corresponding to the dark current is subtracted from current output from the photodiode to detect the optical current. Thus, the detection of the light intensity and the like is performed. However, in the sixth embodiment, focusing on the characteristic of the dark current generated in the photodiode, actuation of the capsule endoscope 132 outside the body of the subject 1 is prevented by positively applying the dark current.

Figure 19:
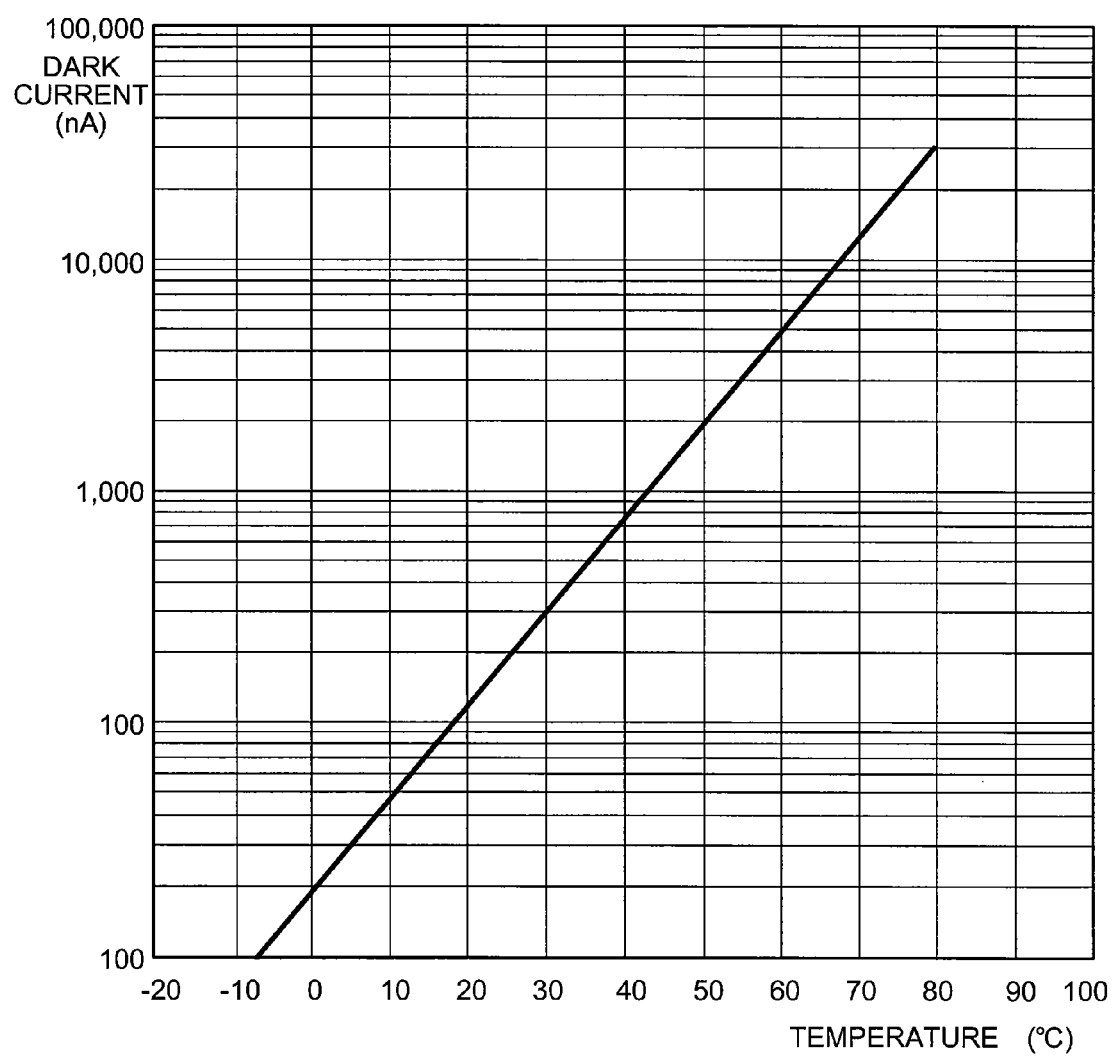
FIG. 19 is a schematic graph showing temperature dependency of intensity of dark current of the photodiode.

The temperature dependence of the dark current will be explained next. FIG. 19 is a graph showing an example of the temperature dependence of intensity of the dark current. The graph shown in FIG. 19 shows a result obtained for general photodiodes, and although the graph does not necessarily correspond with that of the photodiode 135, it can be regarded as approximately the same in terms of tendency of the temperature dependence.

As shown in FIG. 19, the dark current has inclination to increase the intensity according to increase of temperature. More specifically, between dark current Id (nA) and ambient temperature T (° C.), there is a relationship expressed as $$\mathrm{Id} \propto e^T \tag{1}$$

and it is clear that a value of the dark current abruptly increases when the temperature increases, from the graph shown in FIG. 19.

The temperature inside the body of the subject 1 into which the capsule endoscope 132 is to be introduced and the temperature outside the body of the subject 1 is greatly different, and for example, while the temperature inside the subject 1 is about 35° C. to 37° C., the temperature outside the subject 1 is about 10° C. to 20° C., although it depends on an environment. Therefore, in the radio in-vivo information acquiring system according to the sixth embodiment, focusing on the temperature difference between inside and outside the subject 1, the capsule endoscope 132 is prevented from being unintentionally actuated outside the body of the subject 1 by applying the dark current of the photodiode as a detector for the temperature difference. Specifically, understanding the temperature dependence of the dark current of the photodiode 135 that is provided in the dark current detecting unit 133, when dark current corresponding to the temperature inside the subject 1 is detected, the driving controller 34 controls to drive each component in the capsule endoscope 132. More specifically, by the driving controller 34 controlling power supply to the system control circuit 32, the system control circuit 32 controls operation conditions of each component so as to operate according to a predetermined operation method.

Figure 20:
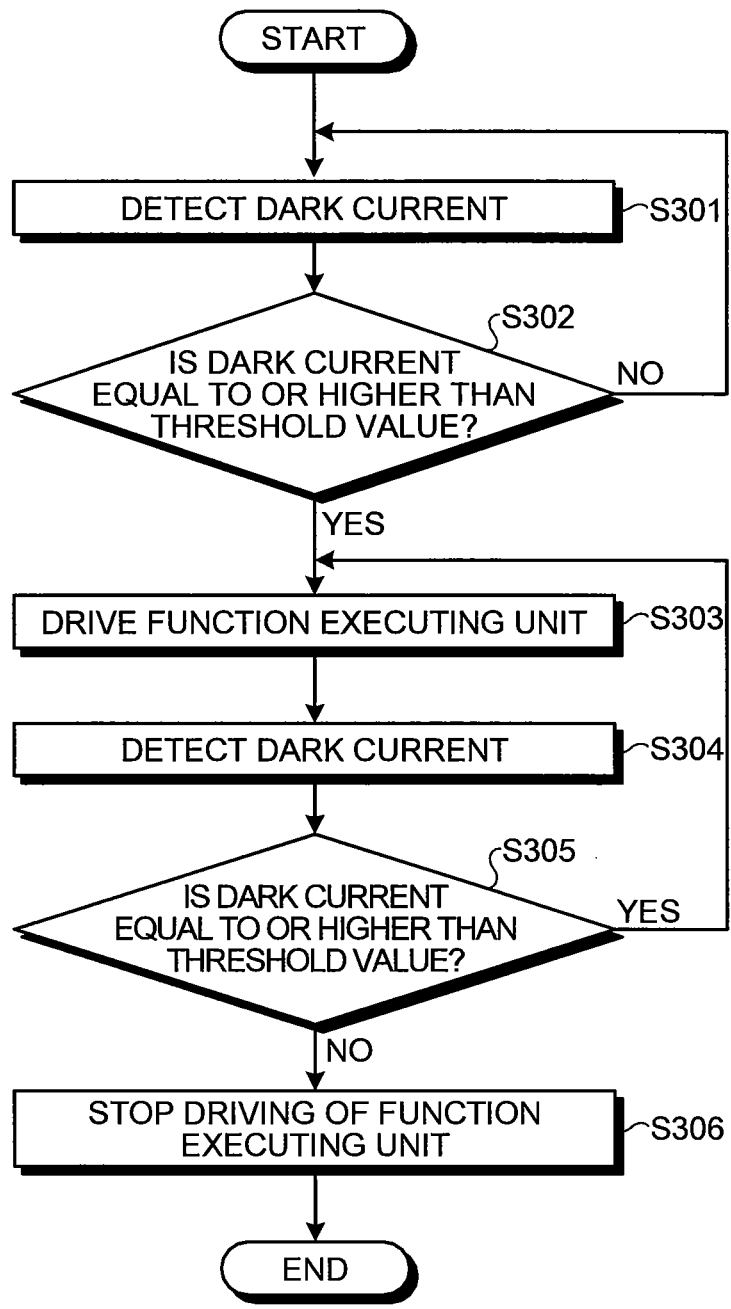
FIG. 20 is a flowchart for explaining an operation of the capsule endoscope according to the sixth embodiment.

Operation of the capsule endoscope 132 according to the sixth embodiment will be explained next. FIG. 20 is a flowchart for explaining the operation of the capsule endoscope 132 according to the sixth embodiment, and explanations will be given hereafter with reference to FIG. 20.

First, the dark current detecting unit 133 detects dark current generated in the photodiode 135 (step S301). The detected dark current is output to the driving controller 34, and the driving controller 34 determines whether a value of the dark current is equal to or higher than a threshold (step S302). The threshold used at this step is, for example, a value corresponding to the temperature inside the body of the subject 1. When the value of the dark current is lower than the threshold, the process returns to step S301, and detection of the dark current and determination of values with respect to the threshold are performed.

When the detected dark current is equal to or higher than the threshold, the driving controller 34 determines that the capsule endoscope 132 has been introduced inside the body of the subject 1, and causes the function executing unit (function executing means) to start driving (step S303). The function executing unit starts driving according to the control to execute a predetermined function. In the configuration according to the sixth embodiment, the LED 19 emits light inside the body of the subject 1, the CCD 21 captures the reflected light of the emitted light, and then, the RF transmitting unit 23 modulates image data as necessary to transmit to the outside through the transmitting antenna unit 24.

The dark current detecting unit 133 again detects dark current generated in the photodiode 135 (step S304), and the driving controller 34 determines whether the dark current is equal to or higher than the threshold (step S305). If it is determined that the value of the dark current is equal to or higher than the threshold, it is assumed that the capsule endoscope 132 is still located inside the body of the subject 1, and therefore, the process returns to step S303 to continue to execute the predetermined function.

On the other hand, if it is determined that the value of the dark current is lower than the threshold, it is assumed that the capsule endoscope 132 has been discharged from the body of the subject 1, and therefore, the driving controller 34 stops power supply to the function executing unit to stop driving thereof (step S306). Thus, the operation of the capsule endoscope 132 is finished.

Advantages of the radio in-vivo information acquiring system according to the sixth embodiment will be explained next. First, the capsule endoscope 132 according to the sixth embodiment uses the temperature dependence of the dark current generated in the photodiode 135 to estimate temperature based on the detected dark current, and estimates whether the capsule endoscope 132 is located inside or outside the body of the subject 1 based on the estimated temperature. When it is estimated to be located outside the body of the subject 1 based on a result of the estimation, driving of the capsule endoscope 132 outside the body of the subject 1 is prevented by stopping the driving of the function executing unit such as the CCD 21, provided in the capsule endoscope 132. Therefore, in the capsule endoscope 132 according to the sixth embodiment, unnecessary execution of the function outside the body of the subject 1, for example, acquisition of image data of the outside of the body of the subject 1, can be prevented, thereby preventing waste of power accumulated in the battery 100 and the like.

Moreover, in the sixth embodiment, there is an advantage obtained because of the configuration in which the temperature detection is executed by use of the photodiode 135. Specifically, as shown in FIG. 19 and Equation (1), the value of the dark current increases exponentially with respect to the temperature. Therefore, the dark current detecting unit 133 that applies the photodiode 135 is capable of temperature detection with high accuracy.

For example, when it is assumed that the temperature outside the body of the subject 1 is about 20° C., the temperature inside the body of the subject 1 is 35° C., and the photodiode 135 has the voltage-current characteristic shown in FIG. 19, while the value of the dark current at 20° C. is about 110 nA, the value of the dark current is increased to 500 nA at 35° C. Even if the temperature outside the body of the subject 1 is high as a case when the capsule endoscope 132 is used in the tropics, for example, when the temperature outside the subject is 30° C., the value of the dark current is about 300 nA, and is remarkably different from 500 nA inside the body of the subject 1. Thus, since the value of the dark current remarkably differs inside and outside of the body of the subject 1, if the temperature is detected using the photodiode 135, it is possible to accurately avoid erroneous operations such that the capsule endoscope 132 is actuated even when positioned outside the subject 1.

Furthermore, in the dark current detecting unit 133, there is an advantage of having the configuration in which the photodiode 135 is covered with the light shielding member 136. In photodiodes used as a photoelectric converting device, deterioration in the crystal structure is sometimes caused due to repeated generation of electron-hole pairs at high frequency based on the light irradiation and energy of the irradiated light. However, in the sixth embodiment, because of the light shielding member 136, light does not enter the photodiode 135, and the electron-hole pairs based on incident light is not generated. In addition, since the absolute value of the dark current to be the detected target is considerably low, influence on the crystal structure and the like can be ignored. Therefore, in the sixth embodiment, it is possible to maintain the electrical characteristic of the photodiode 135 at a considerably stable state, and the correlation between the temperature and the dark current maintains a substantially fixed relationship. Thus, since the dark current detecting unit 133 is configured to include the light shielding member arranged around the photodiode 135, fluctuation of the electrical characteristic of the photodiode 135, thereby further certainly preventing the erroneous operations.

Seventh Embodiment

A radio in-vivo information acquiring system according to a seventh embodiment will be explained next. The radio in-vivo information acquiring system according to the seventh embodiment is configured to perform the driving control based on the number of noise pixels caused in image data due to influence of the dark current when the dark current of the photodiode provided in the CCD that acquires images inside the body of a subject increases as the temperature increases.

Figure 21:
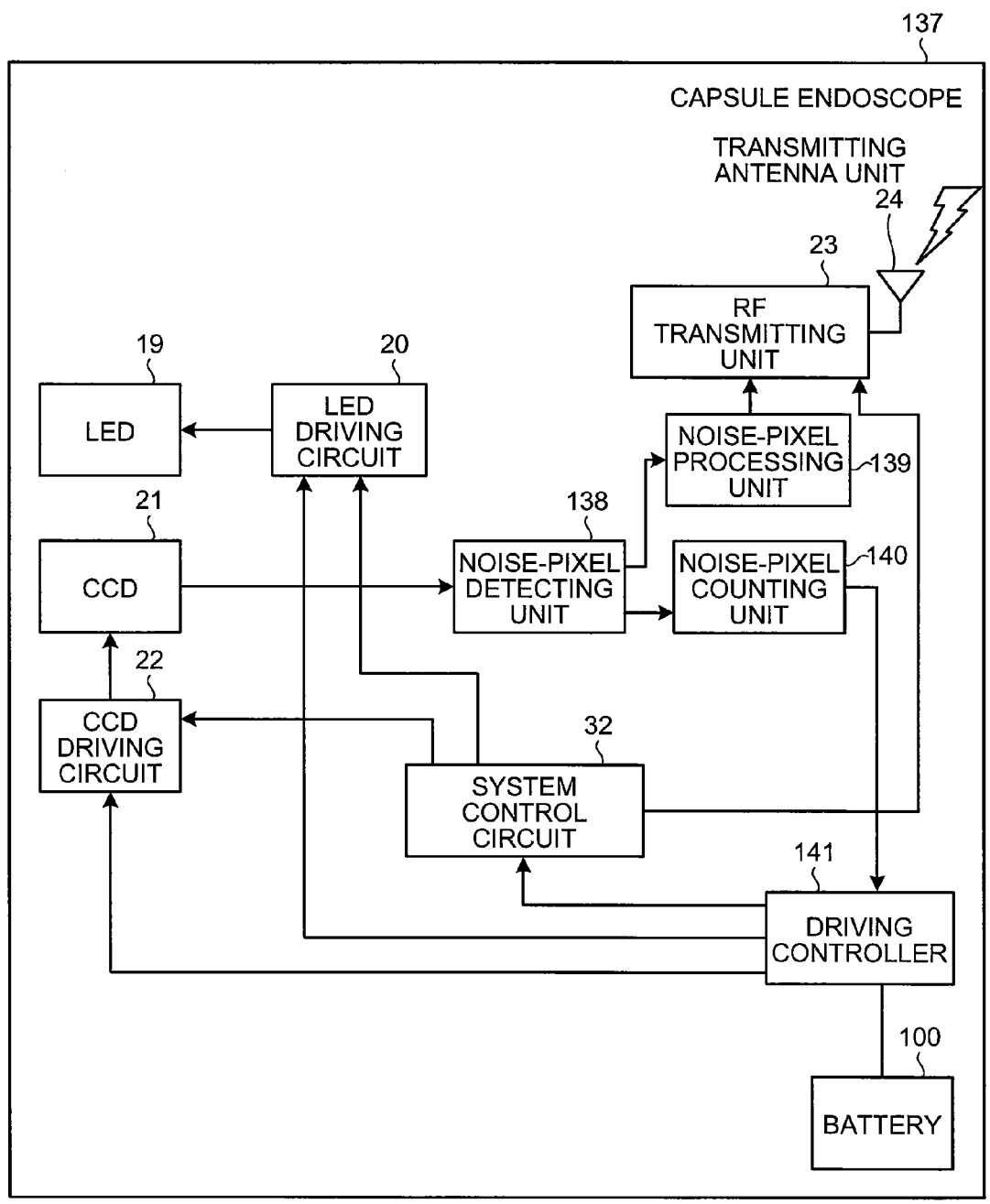
FIG. 21 is a block diagram showing a configuration of a capsule endoscope according to a seventh embodiment.

FIG. 21 is a block diagram showing a configuration of a capsule endoscope 137 constituting the radio in-vivo information acquiring system according to the seventh embodiment. In the seventh embodiment, other components of the radio in-vivo information acquiring system, namely, the receiving device, the display device, and the portable recording medium, have the same configuration and the same functions as those of the sixth embodiment.

As shown in FIG. 21, the capsule endoscope 137 according to the seventh embodiment includes, similarly to the sixth embodiment, the LED 19 that outputs light to illuminate inside the body of the subject 1, the LED driving circuit 20 that controls driving of the LED 19, the CCD 21 that captures the reflected light of the illuminating light, and the CCD driving circuit 22 that controls the driving of the CCD 21. The capsule endoscope 137 further includes the RF transmitting unit 23 that modulates the imaged data acquired by the CCD 21 as necessary to transmit through the transmitting antenna unit 24 by radio communication, and the system control circuit 32 that controls the LED driving circuit 20, the CCD driving circuit 22, and the RF transmitting unit 23. Furthermore, the capsule endoscope 137 includes the battery 100 that accumulates power to drive internal components provided in the capsule endoscope 137 as the function executing unit that execute each predetermined function.

The capsule endoscope 137 according to the seventh embodiment further includes a noise-pixel detecting unit 138 that detects pixels causing noise in the image data acquired by the CCD 21, a noise-pixel processing unit 139 that processes the noise pixels detected in the image data to create image data from which noise is removed. With the noise-pixel detecting unit 138 and the noise-pixel processing unit 139 provided, it is possible to acquire clear image data obtained by removing noise from the image data acquired by the CCD 21.

Moreover, the capsule endoscope 137 according to the seventh embodiment includes a noise-pixel counting unit 140 to which information on the noise pixels detected by the noise-pixel detecting unit 138, and that counts the number of the noise pixels based on the input information, and a driving controller 141 that controls driving conditions of the LED 19, the RF transmitting unit 23, and the like based on the number of the noise pixels counted by the noise-pixel counting unit 140.

The noise-pixel detecting unit 138 detects pixels causing forming noise from among many pixels constituting the image data acquired by the CCD 21. Various detecting mechanisms for noise pixels are known, and the detecting mechanisms include a configuration to detect pixels of which brightness is remarkably high compared to adjacent pixels as the noise pixels, and a configuration to detect pixels having brightness equal to or higher than a predetermined threshold as the noise pixels. The noise-pixel detecting unit 138 has a function of generating information by adding position information of the noise pixels to the image data acquired b the CCD 21 after detection of the noise pixels, and of outputting the information to the noise-pixel processing unit 139 and the noise-pixel counting unit 140.

The noise-pixel processing unit 139 generates image data in which the brightness of the noise pixels is corrected to an appropriate brightness based on the information output from the noise-pixel detecting unit 138, and outputs the generated image data to the RF transmitting unit 23. The generation of the image data is performed by, for example, taking the average of the brightness of pixels positioned around the noise pixel, and by correcting the brightness of the noise pixel to the average.

The noise-pixel counting unit 140 counts the number of the noise pixels in the image data based on the information output from the noise-pixel detecting unit 138. Specifically, since the information generated by the noise-pixel detecting unit 138 includes the position information of the noise pixels, the noise-pixel counting unit 140 counts the number of the noise pixels based on the position information, and has a function of outputting the number of the noise pixels counted to the driving controller 141.

The driving controller 141 controls driving conditions of components of the capsule endoscope 137 other than the CCD 21, the CCD driving circuit 22, the noise-pixel detecting unit 138, and the noise-pixel counting unit 140. Specifically, the driving controller 141 controls the driving conditions of each component by supplying power when the number of the noise pixels becomes equal to or more than a threshold that is determined based on the temperature inside the body of the subject 1, and by stopping power supply when the number is less than the threshold. By executing the driving control by the driving controller 141, actuation of the capsule endoscope 137 outside the body of the subject 1 is prevented.

Figure 22:
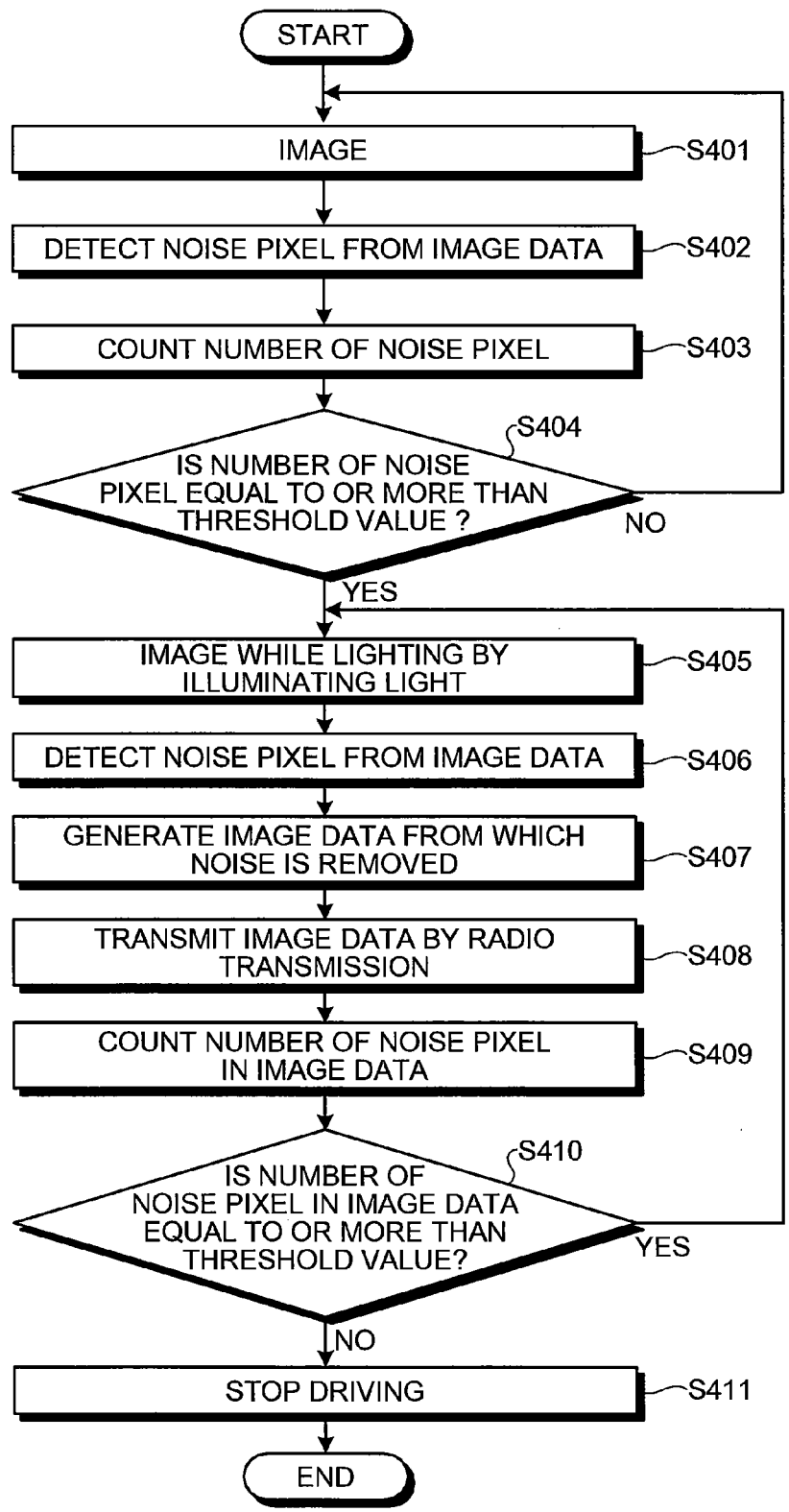
FIG. 22 is a flowchart for explaining an operation of the capsule endoscope according to the seventh embodiment.

An operation of the capsule endoscope 137 according to the seventh embodiment will be explained next. FIG. 22 is a flowchart showing the operation of the capsule endoscope 137, and explanations will be given hereafter with reference to FIG. 22. First, the CCD 21 performs an imaging operation based on the control of the CCD driving circuit 22, to acquire image data (step S401). At this step, the LED 19 does not emit illuminating light during imaging. The acquired image data is output to the noise-pixel detecting unit 138.

The noise-pixel detecting unit 138 detects the noise pixels constituting a noise component in the image data (step S402). Information on the detected noise pixels is output to the noise-pixel counting unit 140. At this step, although the information can be output also to the noise-pixel processing unit 139, in a viewpoint of lowering the power consumption, it is preferable that the driving of the noise-pixel processing unit 139 is stopped at this step, and therefore, the information is not output to the noise-pixel processing unit 139.

The noise-pixel counting unit 140 then counts the number of the noise pixels present in the image data (step S403). The number of the noise pixels counted is output to the driving controller 141. The driving controller 141 determines whether the number of the noise pixels is equal to or more than a threshold set in advance (step S404). When it is determined that the number of the noise pixels is less than the threshold, the process returns to step S401 again to repeat the above operation.

When it is determined to be equal to of more than the threshold, the driving controller 141 supplies power to each component such as the LED 19, to start driving of each component. Namely, the LED emits the illuminating light, and the CCD 21 performs acquisition of image data on the reflected illuminating light (step S405). The noise pixels are detected from the acquired image data (step S406), and based on the information generated by the noise-pixel detecting unit 138, the noise-pixel processing unit 139 generates image data from which noise is removed (step S407). The RF transmitting unit 23 modulates the generated image data as necessary and outputs the clear image data from which noise is removed to the outside through the transmitting antenna unit 24 (step S408).

On the other hand, the information on the noise pixel detected at step S406 is output to the noise-pixel counting unit 140, the noise-pixel counting unit 140 counts the number of pixels (step S409), and the driving controller 141 determines whether the number of pixels is equal to or more than the threshold again (step S410). When it is determined to be equal to or more than the threshold, the process returns to step S405 to repeat the above operation.

When it is determined that the number of noise pixels is less than the threshold, the driving controller 141 stops power supply to all components in the capsule endoscope 137 to stop driving thereof (step S411). Thus, the operation of the capsule endoscope 137 according to the seventh embodiment is finished.

As described above, in the radio in-vivo information acquiring system according to the seventh embodiment, the capsule endoscope 137 performs driving control not based the value of the dark current of the photodiode itself, but based on the number of photodiodes of which the value of current generated therein exceeds the threshold among many photodiodes provided in the CCD 21. Generally, the electrical characteristic of photodiodes has temperature dependence, and for example, for a CCD and the like used in a digital camera, it is understood that the number of pixels causing noise increases as temperature increases. In the seventh embodiment, using the temperature dependence of noise intensity of the photodiodes, when the number of noise pixels is less than the threshold, it is determined that the capsule endoscope 137 is located outside the body of the subject 1, and driving is stopped.

Advantages obtained in the radio in-vivo information acquiring system according to the seventh embodiment will be explained next. First, similarly to the sixth embodiment, by performing the driving control using the temperature dependence of the dark current generated in the photodiode, it is possible to prevent the capsule endoscope 137 from driving outside the body of the subject 1 based on the temperature difference inside and outside the body of the subject 1.

Moreover, in the radio in-vivo information acquiring system according to the seventh embodiment, applying an existing configuration, it is possible to achieve temperature detection with a simple configuration. In other words, the CCD 21 used to detect the temperature has already been provided conventionally to acquire images inside the body of the subject 1. Furthermore, the noise-pixel detecting unit 138 has been provided conventionally to remove, at the time of acquiring image data inside the body of the subject 1, noise components from the image data acquired by the CCD 21.

By applying the existing components, a component to be newly provided for temperature detection is only the noise-pixel counting unit 140, and the noise-pixel counting unit 140 can be configured simply with an electric circuit and the like that counts the number of noise pixels from the information on the noise pixels, to detect temperature. Therefore, even if the noise-pixel counting unit 140 is newly provided, the size of the capsule endoscope 137 is not large-sized, and manufacturing cost is also kept at the same amount as the conventional system, as in a case in which the temperature sensor is separately provided.

Furthermore, in the radio in-vivo information acquiring system according to the seventh embodiment, there is an advantage in that erroneous detection can be suppressed by using many photodiodes provided in the CCD 21. By using many photodiodes, even if a change in the electrical characteristic occurs in a part of the photodiodes, a reliable detection result can still be obtained as a whole.

Eighth Embodiment

Figure 23:
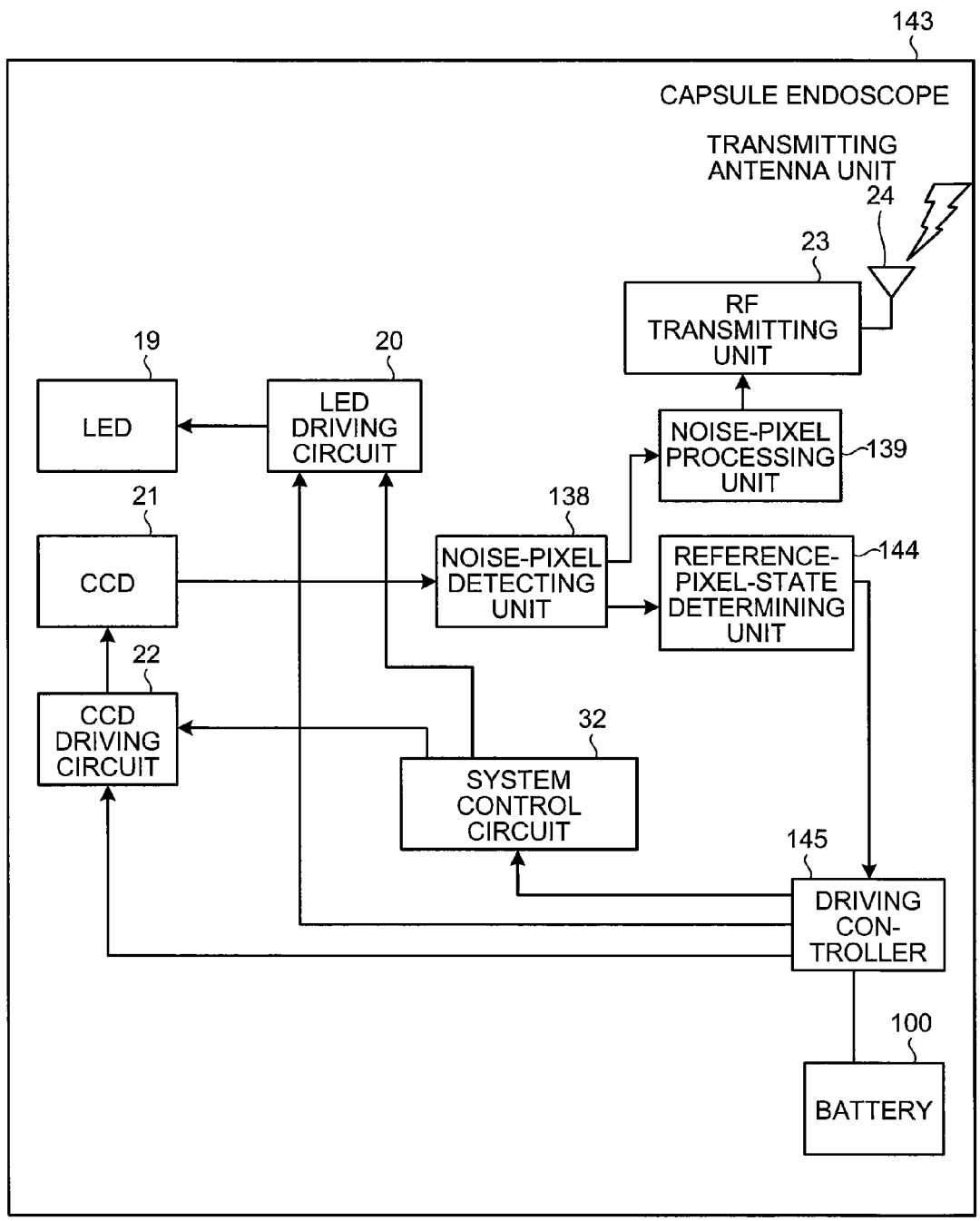
FIG. 23 is a block diagram showing a configuration of a capsule endoscope according to an eighth embodiment.

A radio in-vivo information acquiring system according to an eighth embodiment will be explained next. FIG. 23 is a block diagram showing a configuration of a capsule endoscope 143 according to the eighth embodiment. Similarly to the seventh embodiment, other components of the radio in-vivo information acquiring system according to the eighth embodiment, namely the receiving device, the display device, and the portable recording medium have the same configuration and the functions.

As shown in FIG. 23, in the capsule endoscope 143 according to the eighth embodiment, while basic components are common with the capsule endoscope 137 according to the seventh embodiment, instead of the noise-pixel counting unit 140, a reference-pixel-state determining unit 144 and a driving controller 145 that performs driving control based on a result of determination by the reference-pixel-state determining unit 144 are provided.

The reference-pixel-state determining unit 144 determines whether a plurality of reference pixels determined in advance are detected as noise pixels in the image data acquired by the CCD 21. Specifically, for example, since the noise-pixel detecting unit 138 has a function of adding the position information on the noise pixels to the image data to output, it is determined whether the reference pixels belonging to predetermined positions are noise pixels based on the output information.

Figure 24:
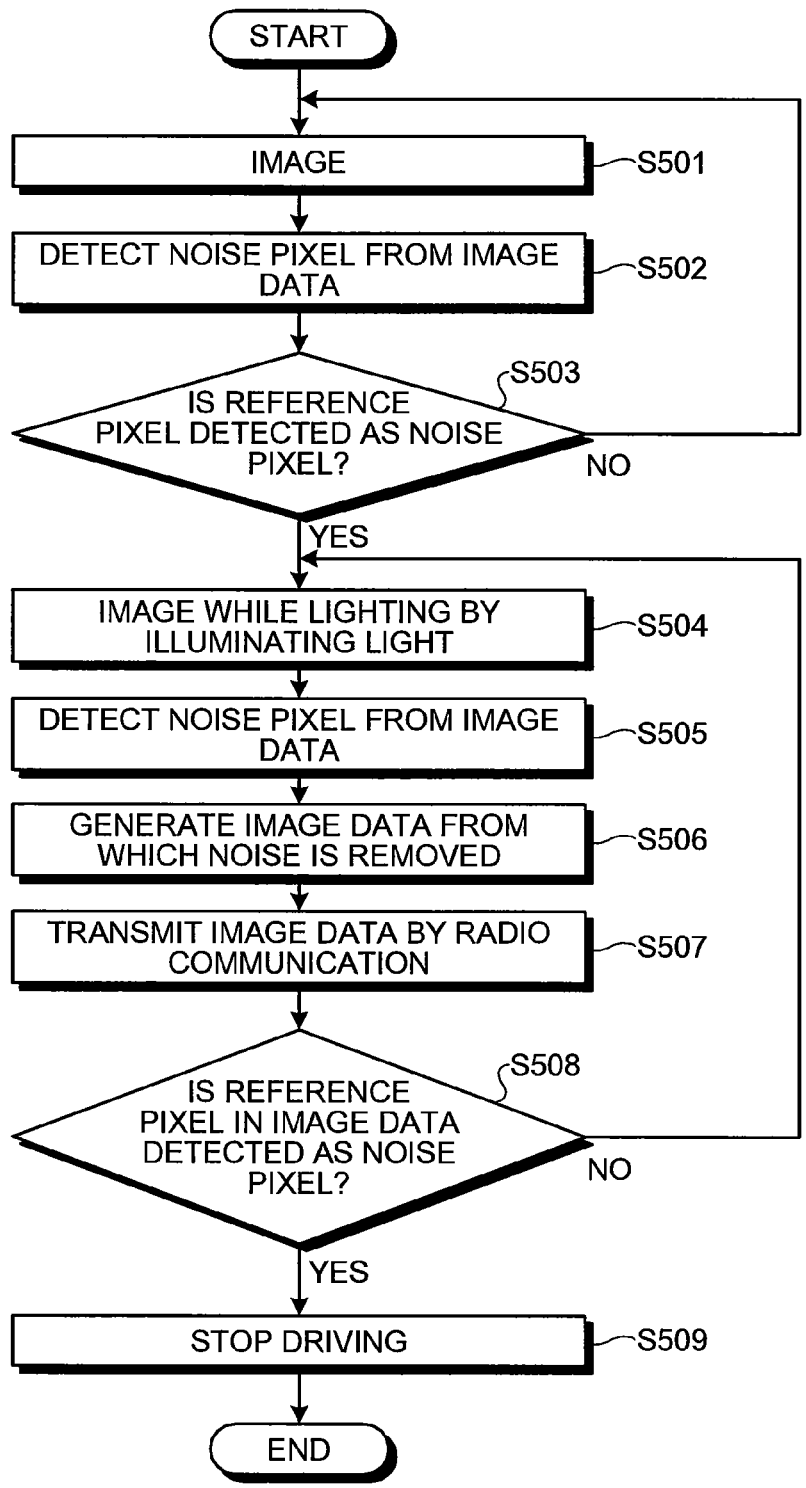
FIG. 24 is a flowchart for explaining an operation of the capsule endoscope according to the eighth embodiment.

An Operation of the capsule endoscope 143 according to the eighth embodiment will be explained next. FIG. 24 is a flowchart for explaining the operation of the capsule endoscope 143 according to the eighth embodiment, and the explanations will be given hereafter with reference to FIG. 24.

First, an imaging operation is performed by the CCD 21 without emitting illuminating light from the LED 19 (step S501), and the noise-pixel detecting unit 138 performs noise pixel detection on the acquired image data (step S502). The reference-pixel-state determining unit 144 determines whether the reference pixels determined in advance are detected as the noise pixels (step S503). If there are plural reference pixels, it is determined that "the reference pixel is detected as a noise pixel" when all of the reference pixels are noise pixels or when the predetermined number of the reference pixels are noise pixels. When it is determined that no reference pixel is detected as a noise pixel, the process returns to step S501 again and the above operation is repeated.

When the reference pixel is detected as the noise pixel, the driving controller 145 supplies power to each component such as the LED 19 to start driving of each component. Specifically, imaging is performed while the LED 19 emits illuminating light (step S504), a noise component is detected from the image data (step S505), and the noise-pixel processing unit 139 generates image data from which the noise is removed (step S506) and transmits the image data by radio communication (step S507).

It is again determined whether the reference pixel in the image data acquired at step S504 is detected as the noise pixel (step S508). When the reference pixel is detected as the noise pixel, the process returns to step S504 and the above operation is repeated. On the other hand, when the reference pixel is not detected as the noise pixel, the driving controller 145 stops power supply to each component such as the LED 19 to stop driving of each component (step S509). Thus, the operation of the capsule endoscope 143 according to the eighth embodiment is finished.

As in the eighth embodiment, it is possible to detect temperature based on whether noise occurs in specific reference pixels. In other words, each of the photodiodes provided in the CCD 21 has temperature dependence in magnitude of the dark current, and therefore, whether noise is caused is also temperature dependent. Therefore, by detecting whether a certain reference pixel causes noise, it is possible to detect the temperature of the capsule endoscope 143, and further, to detect whether the capsule endoscope 143 is introduced inside the body of the subject 1. Thus, in the radio in-vivo information acquiring system according to the eighth embodiment, similarly to the sixth and the seventh embodiments, it is possible to prevent the capsule endoscope 143 from driving outside the body of the subject 1, thereby lowering the power consumption and the like.

To make the temperature at which the reference pixel causes noise and the temperature inside the body of the subject 1 correspond with each other, it is necessary to make some arrangement in a specific configuration of the photodiodes. For example, it is preferable to adopt such a formation that an electric field concentrates on a specific region when reverse voltage is applied.

While the present invention has been explained using the sixth to the eighth embodiments above, the present invention is not limited to the above, and those skilled in the art can think of various embodiments, modification, and application. For example, in the sixth embodiment, the capsule endoscope 132 acquires images inside the body of the subject 1 with the LED 19, the CCD 21, and the like provided. However, the body-insertable apparatus to be introduced inside the body of a subject is not limited to this configuration, and, and for example, can be configured to acquire other in-vivo information such as temperature information and pH information. Moreover, the body-insertable apparatus can include an oscillator to acquire ultrasound images inside the subject 1. Furthermore, the body-insertable apparatus can be configured to acquire a plurality of types of information among the in-vivo information.

In addition to the configuration in which only reception of the radio signal output from the capsule endoscope is performed, the receiving device 2 can be configured to transmit a power supply signal to supply power to drive the function executing unit to the capsule endoscope, and can be configured to regenerate the driving power from the power supply signal received at the capsule endoscope. Moreover, a storing unit can be provided in the capsule endoscope, and information can be extracted from the storing unit after the capsule endoscope is discharged from the body of the subject 1.

Furthermore, the threshold temperature is not necessarily set to a value corresponding to a temperature lower than body temperature of the subject 1. For example, when the system is developed for the purpose of imaging a specific affected portion present in the body of the subject 1, and if the specific affected portion has higher temperature than other areas in the subject 1, temperature corresponding to such a temperature can be applicable to the threshold temperature.

Furthermore, while in the sixth to the eighth embodiments, it is configured such that the driving power is supplied to each component such as the LED 19 through the driving controller, it can be configured such that the power is directly supplied to each component. Moreover, a component controlled by the driving controller can be a part of the components in the capsule endoscope, such as the RF transmitting unit 23 only. The driving controller can be provided in the system control circuit 32. Moreover, while in the sixth to the eighth embodiments, the driving controller is configured to stop the driving of each component both before the capsule endoscope is introduced into the body of the subject and after being discharged from the subject, the driving controller can be configured to perform a stop control only either of the cases. This is because even if the stop control is performed in only either one of the cases, it is still possible to prevent acquisition of unnecessary image data and to lower the power consumption compare to the conventional technologies.

Furthermore, in the sixth to the eighth embodiments, an example in which the CCD is used as an imaging unit has been explained, it can be configured to use, for example, a CMOS other than the CCD. Also in the case of the CMOS, it is configured to be provided with the photoelectric converter such as a photodiode, therefore, it is applicable to the present invention similarly to the case of the CCD. Furthermore, while in the sixth to the eighth embodiments, an example in which the photodiode is used as the photoelectric converter has been explained, it can be configured to use, for example, a phototransistor other than the photodiode. In other words, materials other than photodiodes are also applicable to the present invention as the photoelectric converter, as long as the dark current dependent on temperature is generated therein.

INDUSTRIAL APPLICABILITY

As described above, the body-insertable apparatus according to the present invention is useful for a medical examination device to examine an examined area while being introduced inside a human body, and is particularly suitable for accurately performing collection and transmission of images inside the body of a subject while reducing unnecessary power consumption.

The invention claimed is:

1. A body-insertable apparatus that is used in a state of being introduced inside a body of a subject and that executes a predetermined function inside the body of the subject, comprising:
    a driving controller that controls a driving condition of the predetermined function,
    an information acquiring unit that acquires in-vivo information of an examined area inside the body of the subject;
    a radio unit that modulates a signal relating to the in-vivo information, the signal generated by the information acquiring unit, to transmit the modulated signal by radio communication;
    a power source unit that accumulates driving power to drive the information acquiring unit and the radio unit; and
    a detector that emits light and detects a distance to an object which lies in a path of the light as a distance to the examined area based on the light reflected from the object, wherein
    the driving controller includes a supply controller that controls supply of the driving power from the power source unit to the radio unit based on a result of detection by the detector.

* * * * *

UNITED STATES PATENT AND TRADEMARK OFFICE
CERTIFICATE OF CORRECTION

PATENT NO.       : 8,449,458 B2                                             Page 1 of 1
APPLICATION NO. : 11/571504
DATED            : May 28, 2013
INVENTOR(S)      : Shimizu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1692 days.

Signed and Sealed this
Eighth Day of September, 2015

Michelle K. Lee
*Director of the United States Patent and Trademark Office*